United States Patent
Zegarelli

(10) Patent No.: US 10,238,478 B2
(45) Date of Patent: *Mar. 26, 2019

(54) ORAL APPLIANCE FOR DELIVERY OF MEDICAMENTS AND/OR OTHER SUBSTANCES

(71) Applicant: Peter John Zegarelli, Sleepy Hollow, NY (US)

(72) Inventor: Peter John Zegarelli, Sleepy Hollow, NY (US)

( * ) Notice: Subject to any disclaimer, the term of this patent is extended or adjusted under 35 U.S.C. 154(b) by 154 days.

This patent is subject to a terminal disclaimer.

(21) Appl. No.: 15/176,628

(22) Filed: Jun. 8, 2016

(65) Prior Publication Data

US 2016/0278901 A1 Sep. 29, 2016

Related U.S. Application Data

(60) Division of application No. 14/743,403, filed on Jun. 18, 2015, now Pat. No. 9,649,182, which is a
(Continued)

(51) Int. Cl.
*A61C 19/06* (2006.01)
*A61C 13/00* (2006.01)
(Continued)

(52) U.S. Cl.
CPC .............. *A61C 19/063* (2013.01); *A61B 1/24* (2013.01); *A61B 6/14* (2013.01); *A61B 8/0875* (2013.01); *A61B 10/0051* (2013.01); *A61C 5/90* (2017.02); *A61C 9/004* (2013.01); *A61C 9/0053* (2013.01); *A61C 13/0013* (2013.01); *A61C 19/066* (2013.01); *A61K 8/042* (2013.01); *A61K 9/0053* (2013.01); *A61K 9/0063* (2013.01); *A61K 9/06* (2013.01); *A61K 35/38* (2013.01); *A61Q 11/00* (2013.01); *B29C 64/135* (2017.08);
(Continued)

(58) Field of Classification Search
CPC ..... A61C 19/066; A61C 19/063; A61C 19/08; A61C 5/90; A61C 9/04; B33Y 50/02
See application file for complete search history.

(56) References Cited

U.S. PATENT DOCUMENTS

| | | | |
|---|---|---|---|
| 5,194,003 A | 3/1993 | Garay et al. | |
| 5,711,935 A | 1/1998 | Hill | |

(Continued)

OTHER PUBLICATIONS

International Search Report, ISA/US, dated Nov. 26, 2013.

*Primary Examiner* — Yogesh P Patel
(74) *Attorney, Agent, or Firm* — William D. Schmidt, Esq.; Sorell, Lenna & Schmidt, LLP

(57) ABSTRACT

An oral appliance is provided for delivering a medicament to at least a portion of teeth and/or soft tissue areas inside a mouth. The oral appliance contains an interior surface having a medicament disposed in or on at least a portion of and/or the entire interior surface of the oral appliance. The interior surface of the oral cavity is formed to fit contours of at least the portion of the teeth and/or soft tissue areas inside the oral cavity and is configured for holding the medicament in contact with at least the portion of the teeth and/or soft tissue areas inside the oral cavity to deliver the medicament to strategic areas in need of treatment. In some embodiments, computer, network and computer readable storage media are provided.

16 Claims, 6 Drawing Sheets

Related U.S. Application Data continuation of application No. 13/543,320, filed on Jul. 6, 2012, now Pat. No. 9,089,388.

(51) Int. Cl.

| | | |
|---|---|---|
| *G06T 19/00* | (2011.01) | |
| *B33Y 50/02* | (2015.01) | |
| *A61B 10/00* | (2006.01) | |
| *A61C 9/00* | (2006.01) | |
| *G05B 15/02* | (2006.01) | |
| *G06F 17/50* | (2006.01) | |
| *A61K 8/04* | (2006.01) | |
| *A61K 9/00* | (2006.01) | |
| *A61K 9/06* | (2006.01) | |
| *A61K 35/38* | (2015.01) | |
| *A61Q 11/00* | (2006.01) | |
| *G05B 19/4099* | (2006.01) | |
| *G06T 17/00* | (2006.01) | |
| *A61B 1/24* | (2006.01) | |
| *A61B 6/14* | (2006.01) | |
| *A61B 8/08* | (2006.01) | |
| *A61C 5/90* | (2017.01) | |
| *B29C 64/135* | (2017.01) | |
| *B29C 64/386* | (2017.01) | |
| *B33Y 10/00* | (2015.01) | |
| *B33Y 80/00* | (2015.01) | |
| *B29C 35/08* | (2006.01) | |
| *B29K 105/00* | (2006.01) | |
| *B29L 31/00* | (2006.01) | |

(52) U.S. Cl.
CPC ............ *B29C 64/386* (2017.08); *B33Y 50/02* (2014.12); *G05B 15/02* (2013.01); *G05B 19/4099* (2013.01); *G06F 17/50* (2013.01); *G06T 17/00* (2013.01); *G06T 19/00* (2013.01); *A61C 13/0004* (2013.01); *B29C 35/0805* (2013.01); *B29C 2035/0827* (2013.01); *B29K 2105/0061* (2013.01); *B29L 2031/753* (2013.01); *B33Y 10/00* (2014.12); *B33Y 80/00* (2014.12); *G06T 2210/41* (2013.01)

(56) References Cited

U.S. PATENT DOCUMENTS

| | | | |
|---|---|---|---|
| 6,386,869 B1 * | 5/2002 | Zegarelli | A61C 19/063 433/215 |
| 6,626,669 B2 | 9/2003 | Zegarelli | |
| 6,739,869 B1 | 5/2004 | Taub | |
| 7,766,658 B2 | 8/2010 | Tricca et al. | |
| 8,113,837 B2 | 2/2012 | Zegarelli | |
| 8,585,406 B2 | 11/2013 | Zegarelli | |
| 2004/0015327 A1 | 1/2004 | Sachdeva et al. | |
| 2004/0110110 A1 | 6/2004 | Chishti | |
| 2004/0229185 A1 | 11/2004 | Knopp | |
| 2005/0042210 A1 | 2/2005 | Akai | |
| 2005/0070782 A1 | 3/2005 | Brodkin | |
| 2006/0093982 A1 | 5/2006 | Wen | |
| 2006/0115782 A1 | 6/2006 | Li et al. | |
| 2006/0115790 A1 | 6/2006 | Alon | |
| 2006/0275736 A1 | 12/2006 | Wen | |
| 2009/0117507 A1 | 5/2009 | Abolfathi et al. | |
| 2009/0136893 A1 * | 5/2009 | Zegarelli | A61C 19/063 433/80 |
| 2009/0248184 A1 | 10/2009 | Steingart et al. | |
| 2009/0269720 A1 | 10/2009 | O'Donnell | |
| 2010/0086890 A1 | 4/2010 | Kuo | |
| 2011/0020761 A1 | 1/2011 | Kalili | |
| 2011/0136077 A1 | 6/2011 | De Moyer | |
| 2012/0015316 A1 | 1/2012 | Sachdeva et al. | |
| 2012/0028221 A1 | 2/2012 | Williams | |
| 2012/0214123 A1 | 8/2012 | Zegarelli | |

* cited by examiner

ORAL APPLIANCE FOR DELIVERY OF MEDICAMENTS AND/OR OTHER SUBSTANCES

BACKGROUND

Medicaments may be delivered to patients by a variety of ways including oral, intravenous, intramuscular, inhalation, topical, patches, rectal, subcutaneous or local routes of administration to treat the target site. The method of delivery chosen depends, among other things, upon the condition being treated, desired therapeutic concentration of the medicament and the duration of medicament concentration that must be maintained at the target site.

Recently, there has been considerable interest in delivering medicaments via the oral cavity (e.g., gums, buccal, and sublingual areas, etc.). Delivery to target sites of the oral cavity has several advantages. One advantage is that it allows localized treatment of the teeth, gums and other soft tissues. Another advantage is that the oral cavity has an extensive network of blood capillaries under the mucosa that is particularly suited to provide rapid and effective systemic absorption of systemic medicaments.

Delivery of medicaments to target sites in the oral cavity, unlike the intravenous (IV), intramuscular (IM), and subcutaneous (SC) routes, does not require sterilized hypodermic needles and does not raise concerns about the safe disposal of needles and accidental needle sticks.

Many, if not most, patients experience anxiety and exhibit symptoms of stress when faced with hypodermic injections via the IM, IV, or SC routes. Burning, edema, swelling, turgidity, hardness and soreness at the injection site can often occur.

Non-invasive topical delivery of medicaments to the oral cavity avoids these problems associated with injections. Non-invasive delivery of medicaments to the oral cavity also has the advantage of avoiding digestive first pass metabolism, where enzymatic degradation within the gastrointestinal tract destroys certain medicaments when taken in pill form orally and administered per oral (PO). For example, therapeutic peptides such as insulin, erythropoietin, and human growth hormone do not survive the acidic milieu of the stomach and cannot be administered orally (PO).

Many oral medicaments are commercially available for cosmetic and therapeutic use, which are delivered locally to the oral cavity. These medicaments are formulated as mouthwashes, rinses, toothpastes, dental gels, tooth powder, chewing gum, lozenges, strips and similar products to treat a variety of conditions including preventing dental calculus formation, dental caries, periodontitis and gingivitis, tooth whitening, as well as the elimination of halitosis. While these formulations provide some benefits, they often require a higher dose, do not stay at the target site long enough for adequate delivery of the medicament, can affect non-targeted tissues leading to adverse side effects and are diluted away by saliva also decreasing effectiveness.

Oral appliances that allow non-invasive delivery of medicaments have been developed that have a reservoir to hold liquid medicaments to be delivered. These oral appliances are available in universal sizes to generically fit adults or are custom made for a precise fit to the teeth and gums of the individual patient. To whiten teeth, these oral appliances are becoming increasingly popular as over-the-counter tooth whitening systems or as part of a treatment plan from dental professionals.

Many oral appliances require the patient or dental professional to fill the reservoir with the liquid medicament. This can be costly and time consuming, and can be very messy with bulky dispensers requiring dexterity particularly when the patient is filling the oral appliance by himself/herself in the confines of their home. This leads to poor patient compliance and the failure of the treatment itself. Often the liquid medicament held by the oral appliance undesirably leaks out of the oral appliance and contacts off target areas of the mouth causing unwanted treatment of these non-targeted areas often with deleterious side effects such as burning, stinging and irritation and altered taste sensations. Sometimes medicament can leak out of the appliance and the patient will swallow the medicament into the gastro-intestinal tract—not a desirable outcome. This loss of medicament may lead to reduced efficacy in the treatment.

Based on the above, new oral appliances are needed that improve delivery of the medicament to the target site. Oral appliances that can be easily manufactured, are preloaded and pre-dosed with medicaments, which reduce unwanted leakage, that are easy and comfortable for the patient and are not limited to the confines of home or a bathroom are also needed.

SUMMARY

New oral appliances are provided that deliver medicaments and/or tissues to an oral cavity in a three dimensional manner. In various embodiments an oral appliance is provided for delivering a medicament to at least a portion of teeth and/or soft tissue areas inside a mouth. The oral appliance contains an interior surface having a medicament disposed in or on at least a portion of and/or the entire interior surface of the oral appliance. The interior surface of the oral cavity is formed to fit contours of at least the portion of the teeth and/or soft tissue areas inside the oral cavity and is configured for supporting and holding the medicament in contact with at least the portion of the teeth and/or soft tissue areas inside the oral cavity to deliver the medicament. In various embodiments, the oral appliance is monolithic or a single piece and the interior surface custom fit and formed to fit contours of the teeth and/or soft tissue areas inside the oral cavity of a patient in need of treatment. Unlike prior art devices, the device of the present application has the medicament and/or cells as part of the device and the medicament and/or cells are not removable from it. In certain embodiments, the oral appliance comprises, consists essentially of or consists one, two, three, four, five or oral appliances.

In certain embodiments, the material of the oral appliance is a polymer gel, a hydrogel, a brush polymer or a combination thereof. In some embodiments, the hydrogel comprises, consists essentially of or consists of an amount from about 10% to about 90% by weight, from about 20% to about 80% by weight, from about 30% to about 70% by weight, from about 40% to about 60% by weight and the medicament comprises, consists essentially of or consists of an amount from about 0.01% to about 50%, from about 0.1% to about 20% by weight, from about 0.5% to about 10%, from about 1% to about 7% by weight.

In some embodiments, the oral appliance is constructed from a digital data set representing at least a portion of or all of the teeth and/or soft tissue areas inside the oral cavity.

In some embodiments, there is an oral appliance for delivering a medicament to at least a portion of teeth and/or soft tissue areas inside an oral cavity, the oral appliance comprising an interior surface having a medicament disposed in or on at least a portion of and/or all of the interior surface of the oral appliance, the interior surface being formed to fit contours of at least the portion of the teeth and/or soft tissue areas inside the oral cavity and being configured for holding the medicament in contact with at least the portion of the teeth and/or soft tissue areas inside the oral cavity to deliver the medicament thereto.

In some embodiments, there is a method of delivering a medicament to the teeth and soft tissues inside the oral cavity, the method comprising: providing an oral appliance comprising an interior surface having a medicament disposed in or on at least a portion of and/or all of the interior surface of the oral appliance, the interior surface being formed to fit contours of at least the portion of the teeth and/or soft tissue areas inside the oral cavity and being configured for supporting and holding the medicament in contact with at least the portion of the teeth and/or soft tissue areas inside the oral cavity to deliver the medicament.

In some embodiments, there is a computer implemented method of making an oral appliance, the method comprising: creating a digital record of a patient's oral cavity which is called the Base Image (BI). The BI can be obtained by the conventional analog method of taking an impression of the patient's mouth with common impression materials such as alginate, polyvinyls, silicones or other such materials or may be taken with various scanning devises for a more direct digital record of the topography of the patient's mouth. With the analog method either the impression would be poured with dental stone and the positive model would be scanned or the impression itself, the negative, would be scanned yielding a digital record of the BI. From the Base Image, which is a permanent record of the topography of the patient's mouth and would be digitally stored for future iterations of appliances, computerized program manipulations are made to create the first digital image (Dig1) of at least a portion of the teeth, and/or soft tissue of the oral cavity. Dig1 is an additive process in which programmatically the platform appliance image is digitally layered over the Base Image (BI). Dig1 is the platform carrier for delivering medicaments and/or cells to the mouth. A second subtractive process of the Base Image, BI, is programmatically made and this image is stored as the second digital image (Dig2). Dig2 is a three dimensional representation of the geographic area to be targeted by the oral appliance. The second digital image (Dig2) is a subtractive process made through program manipulations to treat at least a portion of the teeth and/or soft tissue of the oral cavity in need of treatment; combining the first digital image (Dig1) with the second digital image, Dig2, forms a final third digital image (Dig3) of the oral cavity with the treatment area. It is from this third digital image that the appliance is printed and made virtually through the computer.

In some embodiments, there is a computer system for making an oral appliance pre-loaded with at least one medicament or at least a tissue for grafting, the computer system comprising additive logic encoded in the computer for generating Dig1 data based upon at least a portion of the teeth and/or soft tissues areas of the oral cavity of a patient, the Base Image, data generated using an imaging device. Further logic encoded in the computer for generating Dig2 data by performing a digital segmentation of at least a portion of the teeth and/or soft tissues areas of the oral cavity to determine discrete regions of the oral cavity in need of treatment, logic encoded in the computer for combining the Dig1 data and the Dig2 data to form the Dig3 data from which the oral appliance can be produced, wherein the Dig3 data comprises positions for at least one medicament to be placed at the discrete regions in the oral cavity in need of treatment.

In some embodiments, there is a network based computer system for making an oral appliance pre-loaded with at least one medicament or at least a tissue for grafting, the network based computer system comprising logic encoded in the network for generating Dig1 data representing an additive overlay of at least a portion of the teeth and/or soft tissues areas of the oral cavity of a patient built upon the Base Image. The Base Image (BI) data generated using an imaging device, logic encoded in the network for generating Dig2 data by performing a digital segmentation of at least a portion of the teeth and/or soft tissues areas of the oral cavity to determine discrete regions of the oral cavity in need of treatment, logic encoded in the network for combining the Dig1 data and the Dig2 data to form the Dig3 data from which the oral appliance can be produced, wherein the Dig3 data comprises positions for at least one medicament to be placed at the discrete regions in the oral cavity in need of treatment. Essentially the original image of the mouth (BI) provides the template for creating the additive first digital image (Dig1) and the segmented second digital image (Dig2) through various program manipulations of the base image of the mouth (BI) to form a final treatment third digital image of the mouth (Dig3) from which image the appliance will be fabricated.

In some embodiments, there is a computer readable storage medium storing instructions that, when executed by a computer, cause the computer to: receive BI data from an imaging device, from which image an additive manipulation is performed yielding the Dig1 data representing the platform carrier over at least a portion of the teeth and/or soft tissues areas of the oral cavity of a patient. The BI is then again manipulated to generate a Dig2 data by performing a digital segmentation of at least a portion of the teeth and/or soft tissues areas of the oral cavity to determine discrete regions of the oral cavity in need of treatment. A merging of the additive Dig1 data with the subtractive Dig2 manipulation forms the Dig3 data from which the oral appliance can be produced, wherein the Dig3 data comprises positions for at least one medicament to be placed at the discrete regions in the oral cavity in need of treatment.

In some embodiments, there is an oral appliance for collecting a sample from at least a portion of teeth and/or soft tissue areas inside an oral cavity, the oral appliance comprising an interior surface having an absorptive material disposed in or on at least a portion of and/or all of the interior surface of the oral appliance, the interior surface being formed to fit contours of at least the portion of the teeth and/or soft tissue areas inside the oral cavity and being configured for holding the absorptive material in contact with at least the portion of the teeth and/or soft tissue areas inside the oral cavity to collect the sample therefrom. The absorptive material would follow the geographic areas of the mouth to be tested and would be a Dig2 manipulation of the Base Image.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

FIG. 5 is a representation of segmenting out the gumline from the Base Image.

Figure 1:
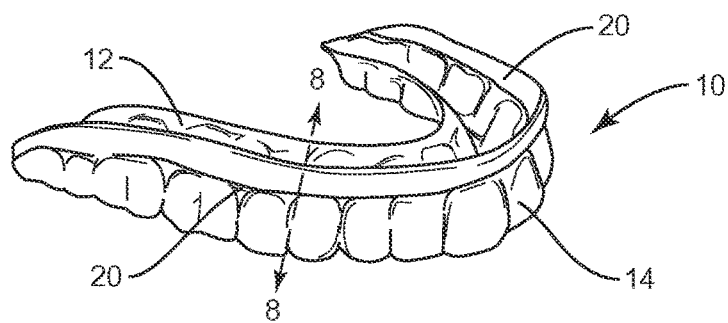
FIG. 1 illustrates an enlarged side view of an embodiment of the oral appliance covering the teeth and/or soft tissues of a patient, the oral appliance without teeth and/or soft tissues inserted in the oral appliance.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a medicament" includes one, two, three or more medicaments.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

Oral Appliance

New oral appliances are provided that can deliver medicaments and/or tissues to at least a portion of the teeth and/or soft tissues inside the oral cavity in a three dimensional way. One advantage of the oral appliance is that it is custom made to fit only one patient. As used herein a "custom fit" oral appliance refers to an oral appliance prepared to correspond to at least a portion of the teeth or all of the teeth and soft tissues of a specific patient. Typically, the custom fit appliance is prepared by a dental care professional (e.g., dentist, oral surgeon, medical doctor, other health care professional, manufacturer, etc.). The custom fit oral appliance can be made from an impression mold, or using an analog or digital image capturing device. The oral appliance provided by this disclosure is not a boil and bite prefabricated device or a stock oral appliance, which can be manipulated by the patient himself/herself with fingers to shape it against the teeth and gums. As opposed to other oral appliances available in the prior art, the appliances provided herein do not contain medicament separately in a cargo area or sponge or placed as a liquid in the oral appliance. The oral appliances disclosed herein are custom fit, disposable, monolithic devices, manufactured in one continuous step, pre-loaded with medicament in or on at least a portion of the interior and/or exterior surfaces of the appliance and can deliver medicaments or graft tissues three dimensionally. In some embodiments, the oral appliance can be transparent. Still another advantage of the oral appliance is that, in various embodiments, it can be easily manufactured and is comfortable for the patient to use. Other advantages of the oral appliances provided by this disclosure include greater efficacy over conventional oral therapies based on two dimensional systems, user convenience, enhanced patient compliance, lower dosage requirements, less dilution of medicament and enhanced applied pressure to gums.

In one embodiment, there is an oral appliance for delivering a medicament to at least a portion of teeth and/or soft tissue areas inside an oral cavity, the oral appliance comprising an interior surface having a medicament disposed in or on at least a portion of and/or all of the interior surface of the oral appliance, the interior surface being formed to fit contours of at least the portion of the teeth and/or soft tissue areas inside the oral cavity and being configured for holding the medicament in contact with at least the portion of the teeth and/or soft tissue areas inside the oral cavity to deliver the medicament thereto.

The soft tissue of the inside of the mouth, includes but is not limited to any soft tissue adjacent or between the teeth, including but not limited to the papilla, tissue of the upper and lower dental arches, marginal gingiva, gingival sulcus, inter-dental gingiva, gingival gum structure on lingual and buccal surfaces up to and including the muco-gingival junction and/or the upper palate and/or the floor of the mouth. In various embodiments, the soft tissue area includes the muco-buccal folds, hard and soft palates, lining mucosa, the tongue and/or attached gingival tissue. In various embodiments, the oral appliance receives one or more teeth including one or more molars, premolars, incisors, cuspids, tooth implant, or combination or portions thereof. In other embodiments, the medicament contained in the oral appliance can be disposed anywhere in or on the interior or exterior surface of the oral appliance adjacent to the gum and/or other soft tissue areas of the oral cavity including the front, back, occlusal surfaces of one or more teeth.

Referring to FIG. 1, an enlarged side view of an embodiment of the oral appliance 10 is illustrated, which has an interior surface 12 and exterior surface 14, both comprising a polymer that can in some embodiments be in gel or hydrogel form. The interior surface 12 contacts one or more teeth and/or soft tissue areas of a patient. The interior surface 12 is custom fit to the individual patient's mouth and configured to receive all or a portion of the teeth and/or soft tissue areas inside the mouth. In this view the interior surface contacts the teeth and soft tissue. Oral appliances include, but are not limited to, oral trays, oral holders, oral covers, or the like that are designed to be placed within the oral cavity. The interior surface 12 and/or exterior surface 14 of the oral appliance contain a medicament disposed in or on the polymer and the medicament can be disposed anywhere within or on the oral appliance as part of a monolithic device. For example, the medicament can be disposed at discrete positions adjacent to the treatment area or uniformly disposed throughout the device. As the interior and/or exterior surface of the oral appliance contacts the oral cavity the medicament is released from the polymer (e.g., gel or hydrogel) by all or parts of the oral appliance contacting the desired treatment site or pressure from the device contacting tissue or fluid at the treatment site (e.g., gums, tissue, teeth, etc.). In some embodiments, all or parts of the oral appliance can degrade over time by the action of enzymes, by hydrolytic action and/or by other similar mechanisms in the oral cavity. In various embodiments, the degradation can occur either at the surface of the oral appliance at discrete positions (heterogeneous or surface erosion) or uniformly throughout the oral appliance (homogeneous or bulk erosion). In some embodiments, all or discrete portions of the interior surface will degrade and release medicament at or near the target site in the oral cavity. The oral appliance will cover at least a portion of the teeth and or gums, by applying the device over axis 8 to cover the area of the teeth and or gums and the oral appliance will be adjacent to the gingival sulcus 20, which will allow the medicament, if desired, to be released from the polymer to this area.

Unlike orthodontic appliances, the present oral appliance is not designed to move teeth. Therefore, a plurality of oral appliances will be configured to hold the teeth in the same position within the appliance. The teeth position will not change. However, the medicament disposed in or on the oral appliance will be in the same or different areas at different stages of the treatment regimen with a variety of oral appliances. Thus, kits containing a plurality of devices can be provided with different treatment stages.

Figure 2:
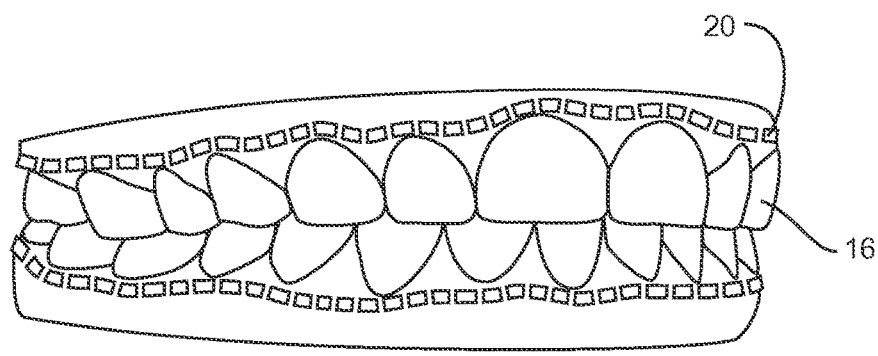
FIG. 2 illustrates an enlarged side view of an embodiment of the oral appliance, where the medicament is shown as infused polymer gel layer that is adjacent to the gingival sulcus region. This view has the teeth and gums loaded in the interior surface of the oral appliance and the oral appliance can be transparent or non-transparent.

FIG. 2 is an enlarged side view of an embodiment of an oral appliance. In this embodiment, the oral appliance is transparent and holds teeth 16 and or gums, which are covered by it. The oral appliance comprises a surface that contains medicament as part of the polymer that in use releases the medicament at or near the gingival sulcus 20.

Figure 3:
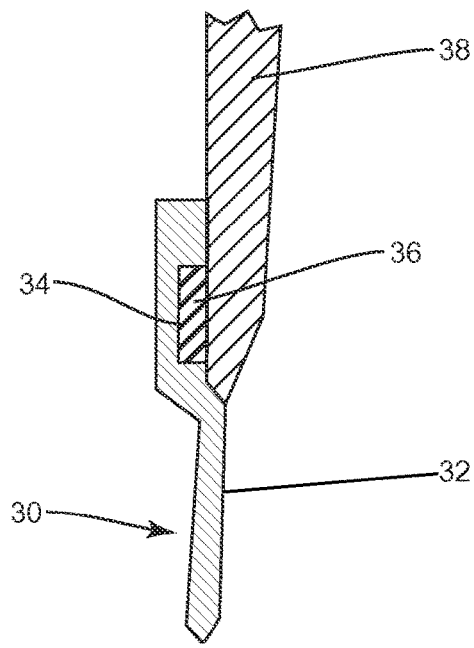
FIG. 3 illustrates a cross section of an embodiment of an oral appliance as a dental oral appliance having the medicament in a hydrogel layer.

FIG. 3 illustrates an enlarged cross sectional view of the portion of the oral appliance 30 and its contact points surrounding a tooth 32 and an interior surface 34 having at least a medicament infused polymer gel layer 36 which extends up and contacts the gingival sulcus region 38. The oral appliance is one piece and does not have the medicament inserted into it. It will be understood that the medicament can be disposed throughout the interior and/or exterior of the device that contacts oral tissue. In the embodiment shown in FIG. 3, the interior of the device has one or more medicaments disposed at discrete regions of the interior surface of the device adjacent to the areas to be treated with the medicament (e.g., tooth and/or soft tissue areas).

Figure 4:
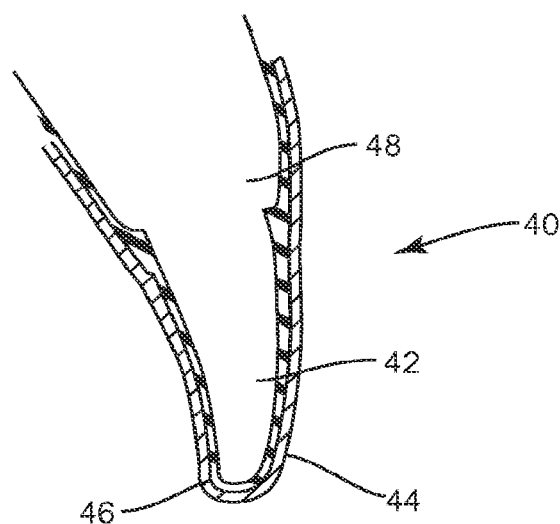
FIG. 4 illustrates an enlarged side cross sectional view of an embodiment of the oral appliance configured to correspond to and cover the tooth and soft tissue areas inside the oral cavity. The interior surface encompasses the polymer gel material having the medicament.

FIG. 4 illustrates an enlarged side cross sectional view of an embodiment of the oral appliance 40 showing an outline of a tooth 42. The oral appliance 40 has an exterior surface 44 and interior surface 46. The interior surface of oral appliance 40 contains a medicament infused polymer gel or hydrogel, which contacts tooth 42 up to gingival area 48. In the embodiment shown, the medicament in the polymer layer extends and contacts the buccal surfaces of the teeth and surrounding gingival tissue and over adjacent gingival tissue on a lingual side of the teeth. In some embodiments, the oral appliance extends over occlusal surfaces of the teeth and/or over lingual surfaces of the teeth in need of treatment.

In various embodiments, oral appliances disclosed herein can be manufactured as more particularly described below. Generally, a patient's mouth is first scanned utilizing a digital data acquisition tool. The data obtained in this manner can be used to form an initial digital record, the Base Image (BI) and that image is retained in a database. A dental professional can also obtain an initial record of the patient's oral cavity by taking an analog impression using alginate or other impression materials from which the analog model or impression will be scanned thus yielding the same BI. It is from this initial record of the patient's mouth, the Base Image (BI) that future oral appliances can be made. This image can be used as a permanent record of the patient's mouth which can then be digitally manipulated yielding a three dimensional representation of the tissues to be treated through the platform carrier, Dig1, and for various treatment modalities, Dig2. A virtual or real oral appliance, Dig3 is thereby formed by merging the additive digital image, Dig1, with the segmentally manipulated image, Dig2, to create the final treatment image, Dig3. The Dig1 image merged with the Dig2 image creates the Dig3 image from which the oral appliance can be created.

The Base Image provides an outline of at least a portion of and/or all the surfaces of the teeth, gingiva and/or other soft tissues, which a dental practitioner may wish to treat. Other soft tissues of the oral cavity include without limitations, the palate, muco-buccal and muco-labial tissues, floor of the mouth, tongue, buccal and labial mucosae, and any other oral tissues. An authorized user can generate Dig1 by using software to create a layer over the teeth and gingiva which tightly approximate these tissues. The original image is now digitally enhanced to have a layer over it. Digital image Dig1 resembles a virtual oral appliance, which can be used to create a real oral appliance. Dig1 is the platform carrier from which all future appliances will be based. With respect to Dig1, the Base Image of the patient's teeth and gums has not been manipulated or modified by the computer at this point, but has had a digitally represented overlay of teeth and soft tissues. The additive process can be varied such that the platform carrier (e.g., oral appliance) can be made thicker in some areas for stiffness and retention, such as over the teeth and thinner in other areas for flexibility and comfort such as over the soft tissues. The platform carrier can also vary chemically in different regions such that it may have a chemically stiffer polymer in one region and a more flexible one in another region. Or the edge of the platform carrier can have a swellable hydrogel to press against the soft tissues and thereby lock in the medications and lock out the saliva thus preventing leakage out and leakage in. Other chemical or elastic formulations and permutations thereof can be mixed and matched to suit a desired result. The current analog model of manufacturing may not yield these variations.

In some embodiments, Dig1 comprises the virtual image of portions of the oral appliance. By using virtual 3D imaging and 3D printing, one can utilize a gradient of physical and chemical characteristics to modify the oral appliance itself. The printer can make portions of the oral appliance thicker for stiffness or thinner for flexibility and comfort. This is programmable in the computer system. In some embodiments, the oral appliance can modulate to give stiff or flexible variations while keeping the oral appliance at a uniform thickness.

The digital image is stored in the computer readable data storage media of the computer. Computer readable media, for example, store data that is accessible by a computer, such as magnetic cassettes, flash memory cards, digital video disks, Bernoulli cartridges, random access memories (RAMs), read only memories (ROMs) or the like and may also be used in the exemplary operating environment. Computer readable media does not include signals.

Using computer software, an authorized user can next generate a second digital image referred to as Dig2. The software generating Dig2 includes points or discrete regions on the teeth and/or gingiva as boundaries corresponding to areas in the oral cavity that the dental practitioner may wish to treat. As used herein the "gingival margin area" comprises an area within the oral cavity, which includes the gum line and the attached gingiva, including the sulcus of the gums. The gingival margin area comprises about 2 to 3 mm of tooth above the gum line. In some embodiments, the points or the discrete regions may include buccal surfaces of the teeth, surrounding gingival tissue, occlusal surfaces of the teeth, lingual surfaces of the teeth, and/or adjacent gingival tissue on a lingual side of the teeth. Through software manipulation of the image of a patient's mouth, Dig2 can be subtracted according to point boundaries to a predetermined depth which corresponds to the desired thickness of the layer to be merged with Dig1. For example, in some embodiments, Dig2 can have a thickness layer of about 0.5 mm. The resulting Dig2 image would be as if the dental professional took a scalpel blade and precisely removed the gums or gum line to a depth of 0.5 mm and/or cut the teeth to a depth of 0.5 mm in one piece. This is a subtractive programming of virtual tissue, the slice of which is then merged precisely onto Dig1 in the exact area from which it was virtually removed. It is digital image Dig2, which holds the medicaments required to treat a selected pathology.

Figure 5:
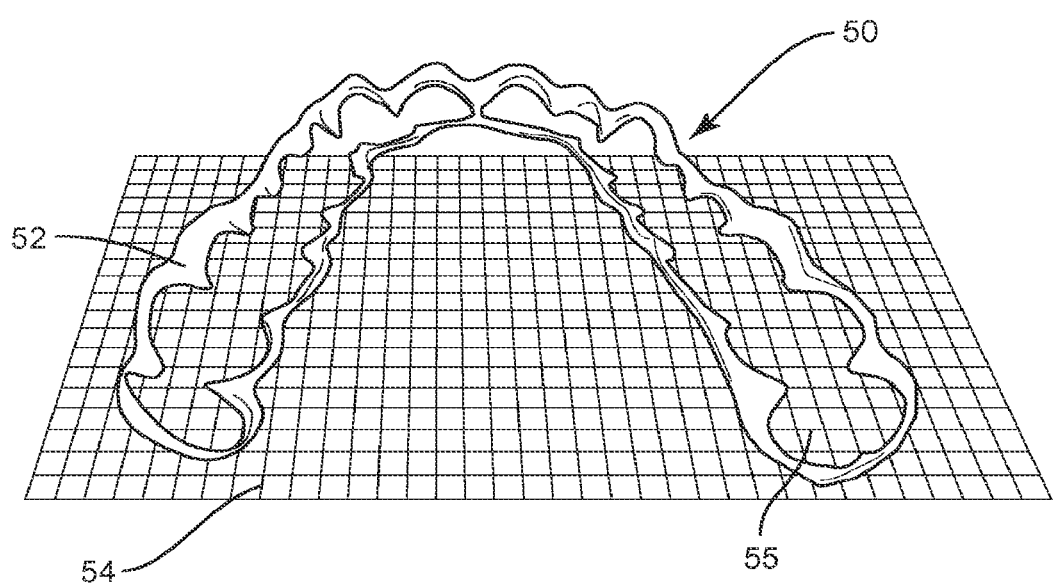
FIG. 5 illustrates an embodiment of a virtual image (Dig2) of the regions along the sulcus (gumline) where the medicament of the oral appliance will be loaded in a polymer gel material. The medicament is disposed at discrete or continuous regions throughout the polymer gel material and corresponds to the regions that will require treatment.

FIG. 5 illustrates a virtual image of the polymer containing the medicament for the oral appliance. This illustrates the subtractive programming. In this case the virtual 3D image 50 can be made by inputting data into the computer as to where the medicament is to be disposed adjacent to the treatment areas of the oral appliance. The computer system can generate the interior surface 52 of the device where medicament will be disposed in the polymer and be adjacent to the treatment area. The 3D image can be generated by subtracting from the Base Image (BI) the soft and/or hard tissues to be treated in a precise pattern, yielding an image of the targeted area, Dig2, to be merged with the original Dig1 platform device image. In some embodiments, the virtual 3D image 50 of the oral appliance will not have a floor to it 55. This is because, in some embodiments, the 3D image generated will only have the discrete regions where the medicament is to be disposed (Dig2). The remainder of the virtual image of the device can be constructed using a spatial geometric pattern 54 that can be used to add the virtual 3D image of the floor of the oral appliance and the exterior surface of the oral appliance. This includes height, width and depth to the virtual image. By utilizing the Dig2 software, a treatment system can be created in which medicaments can be delivered to targeted teeth and/or tissues in a precise three dimensional manner. To date, previous systems for delivering medicaments to the oral cavity have been two dimensional. For example rinses, pastes and lotions, delivered with either a finger, an applicator, toothbrushes, trays or other oral appliance systems, either pre-loaded or patient loaded with medicaments, all wash or coat the teeth and/or tissues vertically and laterally. By adding the dimension of depth to the vertical and lateral dimension, an oral appliance modeled upon Dig2 can deliver medicaments also in a third dimension. The above Dig2 image is a precise subtraction of the targeted tissue accomplished through computer programming, which is then saved to be used as further described below.

Once digital image Dig1 and digital image Dig2 have been generated, they can be merged via computer modeling to generate a third and final digital image, Dig3. In this manner, a virtual platform carrier oral appliance (Dig1) generated on the BI can be combined with a virtual digital image of the treatment area generated based on Dig2 such that the Dig2 image is precisely merged onto the Dig1 platform appliance on the inside of the Dig1 oral appliance to correspond to the exact area from which it was removed. As a result, through an additive process Dig1 can be merged with a subtractive process Dig2 to create a final computer enhanced image Dig3 which is a unique virtual three dimensional image of the oral appliance containing all or a portion of the oral appliance that contains medicament in the areas adjacent to the treatment areas of the oral cavity that are unique to a given patient.

In some embodiments, it is contemplated that only the surfaces of the teeth will be treated and not the gums or only the gums will be treated. Teeth bleaching and caries prevention are examples of such processes.

Generating oral appliances that can provide a three dimensional treatment can be used effectively for providing different therapies for many pathologies of the oral cavity. In other embodiments, a bulge can be placed on the exterior surface of the oral appliance, which would correspond to the lower jaw and the lingual aspect, which faces the floor of the mouth and the lingual veins. In this process Dig1 is obtained as before, however Dig2 would be created through the additive process of creating a bulge upon the exterior surface of Dig1. The bulge generated with Dig2 can hold medicaments to be absorbed directly into the blood stream via the vasculature of the floor of the mouth, specifically the lingual veins by extending out from the tray under the tongue and pushing against the lingual veins. Based on the direct absorptive properties to the blood stream, oral appliances having an external surface having a bulge can be useful in delivering systemic drugs to the body to treat many other diseases.

In another aspect, a virtual oral appliance Dig3 can be generated, which can be used by a dental professional to treat halitosis. The tongue has a rough surface due to the papillae on the tongue. This roughness creates millions of tiny spaces among the papillae which harbor microorganisms which frequently cause halitosis. In this aspect, the palate cover and the palatal aspects of the upper jaw form the external surface of the Dig1 virtual oral appliance. As a result, the Dig2 virtual oral appliance can be generated by adding a roughened surface, Velcro like in texture, which would include medicaments to treat the volatile sulfur compounds produced by the microorganisms harbored among papillae and which cause halitosis. A virtual Dig3 oral appliance generated based on the resulting merger of Dig1 and Dig2 can be used as a scouring pad to treat halitosis. By closing the mouth and rubbing the tongue against the palate and the teeth, a patient could physically cleanse the tongue in a scraping and/or rubbing motion. The rough, scouring pad surface of Dig3 covering the upper jaw and palate (roof of mouth) can physically open and scrub the tiny spaces between papillae thereby allowing the simultaneous introduction of medicaments to kill germs and freshen the breath. This approach provides a different solution from scraping the tongue with a blade, a technique currently used by dental professionals to clean the tongue physically and a process which usually elicits a gag reflex or by the patient using various tongue scraping devices to try to cleanse their tongue usually also eliciting the gag reflex. When one closes their mouth and rubs their tongue against the roof of their mouth there is no gag reflex, thus when rubbing the tongue to the palate with the above described oral appliance one will physically and chemically cleanse their mouth of malodor according to the Dig3 appliance.

Figure 5A:
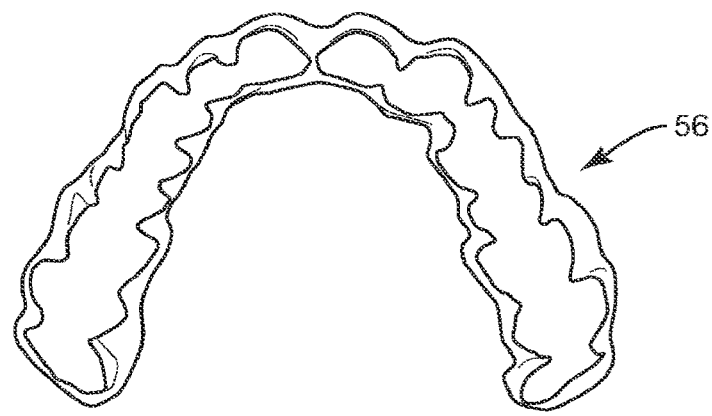
FIG. 5A illustrates an enlarged view of a virtual image (Dig2) of the regions along the sulcus (gumline) where the medicament of the oral appliance will be loaded in a polymer gel material.

FIG. 5A illustrates an enlarged view of a virtual image (Dig2) of the regions along the sulcus (gumline) 56 where the medicament of the oral appliance will be loaded in a polymer gel material.

Figure 5B:
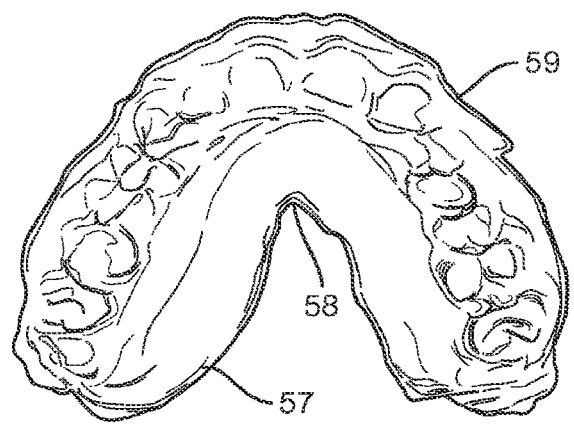
FIG. 5B illustrates an enlarged interior view of a virtual image (Dig1) of the oral appliance that is made by taking the Base Image (BI) of the oral cavity and creating a digital image that additively layers over the oral cavity including the teeth, gums, soft tissue areas and/or the palate. Dig1 does not have the virtual image of where the medicament is to be disposed.

FIG. 5B illustrates an enlarged view of a virtual image (Dig1) of the oral appliance 59 that is made by taking a baseline digital image of the oral cavity and creating a digital image that corresponds to or layers over the oral cavity including the teeth, gums, soft tissue areas and/or the palate. Dig1 does not have the virtual image of where the medicament is to be disposed. The lower portion 58 of the virtual oral appliance corresponds to and will contact portions of the tongue and hard palate 58 as well as the soft palate.

Figure 5C:
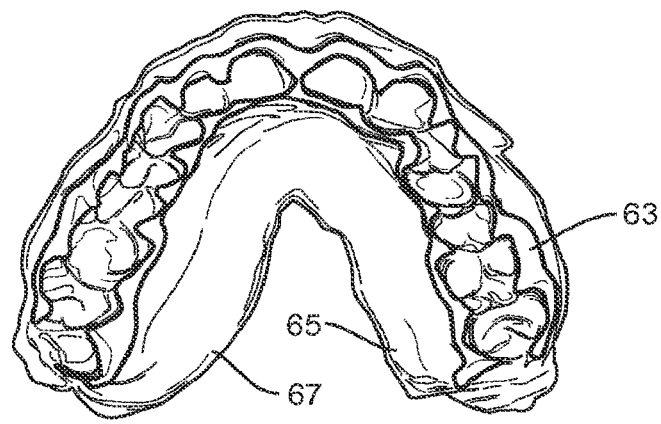
FIG. 5C illustrates an enlarged interior view of a virtual image (Dig3) of the oral appliance. The virtual image is the merging of the additive Dig1 data and the subtractive data of Dig2 from, which the oral appliance can be produced that has regions along the sulcus (gumline) where the medicament of the oral appliance will be loaded in a polymer gel material.

FIG. 5C illustrates an enlarged view of a virtual image (Dig3) of the oral appliance. The virtual image is the merging of the additive Dig1 data and the subtractive data of Dig2 from, which the oral appliance can be produced that has regions along the sulcus (gumline) 63 where the medicament of the oral appliance will be loaded in a polymer gel material. The lower portion of the virtual oral appliance corresponds to and will contact portions of the tongue and hard palate as well as the soft palate 65 and 67 along each side of the oral cavity. It is from Dig3 that the oral appliance can be manufactured.

In another embodiment, oral fungal infections can be treated, using the same textured, palatal "scouring pad" (shown as 67 in FIG. 5C) oral appliance that can be generated based on a virtual Dig3 oral appliance obtained as discussed above with respect to halitosis. Fungal infections are often difficult to treat and eliminate. Historically, dental professionals have used antifungal rinses or lozenges to treat fungal infections. A patient afflicted with fungal infections would usually rinse for about a minute and/or suck on a lozenge for a couple of minutes. By utilizing an oral appliance manufactured based on an virtual Dig3 oral appliance, the tongue of a patient can be treated in part as with halitosis, through rubbing and medicating with anti-fungal medications, while the remaining portion of the oral appliance both interior and exterior aspects of which can be used to deliver the same anti-fungal medications to virtually every surface of the oral cavity in a long and sustained manner which is essential in treating fungal infections. In this embodiment, Dig2 can subtractively create a layer for the entire inside of the oral appliance and additively add a layer to the non-palatal portion of the upper oral appliance and the entire outer portion of the lower oral appliance. Both upper and lower oral appliances can deliver medicaments to the entire mouth inside and out. Held by the teeth and gum, the upper and lower oral appliances can release medicaments through passive contact directly to the tissues. When one closes their mouth there is no open space since the soft tissues collapse against each other and the hard tissues, such that the upper and lower appliances will contact all the tissues in a sustained manner. As a result, multiple rinsing and/or use of lozenges required by conventional therapies can be avoided. The fatigue factor frequently associated with rinsing or sucking on lozenges is also avoided.

The methods described herein of developing oral appliances for three dimensional treatment can also find use in many surgical applications. In some embodiments, the boney defect of a cleft palate can be closed by providing graft tissues utilizing the oral appliances of this disclosure. In cleft palates, there is a hole in the bone allowing communication between the mouth and the nose and sinuses. To allow for normal chewing and swallowing, the cleft palate hole must be closed. Initially, a 3-D image of the defect is obtained by digital data acquisition tools, such as X-ray devices, CAT scanners, MRI scanners, coordinate measuring machines, destructive scanners, ultra sound scanners and the like to capture or generate the Base Image. Subsequently, all the soft tissues lining the hole and the adjacent walls of the bone which are thin and defective can be subtracted through subtractive computer manipulations. After subtracting the soft tissue, the desirable boney contours can be generated in a three dimensional manner following the topographical contours of the bone. The resulting digital image (Dig2) for this application can be the entire piece of bone that would be needed to "plug" the hole and fill the cleft palate. As described above, Dig2 can be added to Dig1 to generate a virtual digital image 3 (Dig3) oral appliance. The Dig3 oral appliance can include an irregular shape rising out of its inside and attached to it. In this aspect, the Dig2 portion can be loaded with either live bone tissue or some synthetic bone. In other embodiments, the Dig2 image could be loaded with various layers of live tissue suspended medium to maintain the live tissue and allow the tissue to grow (e.g., water, saline, dextrose, etc.).

In the cleft palate example discussed above, the oral appliance can provide effective treatment in a three dimensional way. In this embodiment, the virtual image of the cleft having a hole (Dig1) can be filled with a virtual image of the plug (Dig2) and the plug is configured to be received by the hole in the oral appliance adjacent to the cleft palate. The Dig3 image will be a combination of Dig1 and Dig2 and then the Dig3 image can be stored on the computer and then the instructions for manufacturing the oral appliance and/or plug can be sent to a 3D printing device.

The 3D printing can be accomplished using multiple print heads of a stereolithography machine (e.g., for example 1, 2, 3, 4 or more printer heads can be available). The first three heads would print the Dig2 portion such that print head 1 can print the sinus tissue or nasal tissue at the base of the oral appliance (e.g., top of the plug), print head 2 which can print the bone in the body of the oral appliance (e.g., body of plug), print head 3 can print the gingiva at the top of the plug and print head 4 would print Dig1 portion (platform carrier) thus completing the Dig3 protocol. To complete the surgical protocol, a second Dig3 can be generated which has the same size and shape as the first Dig3. The resulting Dig3 appliance can be marked at the base with a dye to help the surgeon identify the area of soft tissue that needs to be removed to get to the layer of bone to be treated, basically a surgical guide stent. Once marked, the surgeon could simply cut along the outline and remove the soft tissue. The oral appliance with the live tissue could then be precisely inserted into the mouth and held precisely in place according to the Dig1 image of the teeth. The Dig3 oral appliance could either remain in place or be tacked down with staples or sutures to keep it in place for the entire healing period desired. Once sufficient healing has occurred, the Dig1 portion of the appliance can be removed separating it from, in this case, the gingival tissue at the interface of Dig2 subtracted from Dig1. The cleft palate graft derived in this manner will remain in place.

In other aspects, tooth loss, gingival and bone grafting procedures, implants, placement of regenerative tooth processes can also be addressed by the methods described in this disclosure. In various other aspects, the three dimensional methods described in this disclosure can be useful to treat other diseases or surgical procedures of the body as a whole.

In some embodiments of the applications described above, once the Dig3 virtual oral appliance is generated in whatever iteration, a virtual 3D image is sent to a stereolithography machine with at least two print heads to print or otherwise manufacture a treatment oral appliance. One print head of the stereolithography machine can print the Dig1 portion of Dig3 and the other can print the Dig2 portion of Dig3 simultaneously. Thus, in one step, an entire oral appliance can be monolithically manufactured according to the instruction provided by Dig3. In various embodiments, the print heads can use different chemical compositions. For example, in certain embodiments, the chemical composition for Dig1 portion can be stiffer in order to better hold onto the teeth and gums and be devoid of absorptive qualities while the Dig2 portion can be made of a different chemical composition which has absorptive qualities and can swell more easily. Useful chemical compositions comprise gels, hydrogels, polymer brushes and other swellable chemicals. These can be mixed uniformly with medicament, or alternately infused into Dig2 material after printing of Dig3.

Stereolithography printing allows the two different chemical compositions of Dig1 and Dig2 to combine simultaneously into one manufactured oral appliance, Dig3, without the use of adhesives or mechanical bonding. This is possible because the chemistry to allow the wedding of Dig1 and Dig2 has been worked out prior the manufacture and printing of Dig3. Additionally, since the hydrogel or other chemical used as a matrix for Dig2 is already loaded with the desired medicaments, the entire Dig3 oral appliance can be manufactured in only one sequence. There will be no soaks, dips, baths, sprays, or medicament rinses to load the appliance.

In some embodiments, the computer program uses an axis graph with physical properties on one axis and chemical properties on the other. These data are sent to print heads for manufacturing the device. The different print heads though holding different formulations will have chemical compatibility between them such that when printed simultaneously the formulations will seamlessly meld together as one piece thus allowing the Dig3 oral appliance to be fabricated at one time without the use of adhesives, glues or mechanical locking devises. In some embodiments, the medicament can be loaded and printed concurrently with the overall oral appliance.

With this digital model the oral appliance manufactured in accordance with Dig3 is now ready to be placed in the oral cavity of the patient either in a wet or dry form. The hydrogel portion of the Dig3 oral appliance will expand if dry when wetted or can be already expanded if wet. In either case, the Dig2 portion of Dig3, which is the three dimensional representation of the area to be treated will release its medicaments to the affected area in a three dimensional manner once the oral appliance is inserted. For embodiments, where the one or more polymers used to make the oral appliance comprises a hydrogel, the hydrogel of the Dig3 oral appliance will continuously diffuse out the medicaments along a diffusion gradient until the medicament is all or substantially all released. This phenomenon is similar to a biologic "wicking" caused by the body tissues of the patient, which will always be at a lower diffusion gradient since the tissues will constantly be absorbing the medicaments thus being at the lower end of the diffusion gradient as the tissue absorbs the drug, it may be delivered to the blood stream. In some embodiments, for example, in bleaching medicaments, the medicament will not to any significant extent be delivered to the blood stream as the target tissue area is the teeth.

In various embodiments, the three dimensional model manufactured by stereolithography has the hydrogel loaded for pre-printing with the medicaments either in a liquid form or dried form (e.g., lyophilized) and the medicament can include salts, enantiomers, esters, epimers, or combinations thereof. In the dried form, in some embodiments, the medicaments can become activated when wetted either with a liquid (e.g., saline, water, saliva, blood or other bodily fluid) and then the medicament begins to diffuse out after the oral appliance is applied to the oral cavity.

Once the oral appliances are printed or manufactured by a stereolithography machine, the oral appliances are dried, packed and shipped to a dental professional who will deliver them to the patient with instructions for their use. The patient then performs a single use treatment and thereafter, after treatment, disposes of the oral appliance. A new tray is used for each treatment according to a prescribed regimen.

In some embodiments, oral appliances manufactured according to the three dimensional model described herein can also be utilized to treat periodontal or gum diseases. In gum disease the initial form of the gums is often reddened and swollen. As such, the gums are larger than normal. As they heal, the gums shrink back to their normal, healed state size and become pink and firm. In order to generate a Dig2 system to treat gum diseases, Dig2 can be modified to take into account the anticipated shrinking of the gums to insure that the medicament layer is always in apposition to the diseased tissue. In some embodiments, if the gums are swollen by 2 mm, there can be a two week or 14 oral appliance treatment period. The first oral appliance for use on the first day can have an initial Dig2 thickness of 0.6 mm identified as Dig2A. The second oral appliance, identified as Dig2B, can have a thickness of 0.7 mm and can be used by the patient on the second day. On the third day, the patient can use Dig2C oral appliance, which can have a thickness of 0.8 mm. The process repeats itself until day 14 when the thickness of Dig2N can be 2 mm, thus fully accounting for the shrinkage of the gums and also allowing the medicaments to be always in direct contact with the gums. If this approach were not followed, the patient could end up with a situation where there would either be a gap between Dig2 and the gums or the gums would not shrink completely. This is a progressive system in which the Dig3 oral appliances are manufactured to account for daily and/or weekly changes to the desired therapy. Thus, in certain embodiments, the thickness of surface oral appliance is incrementally configured for treatment of a gum disease. Such a precise approach could not be accomplished with analog devices used in a conventional two dimensional system.

The thickness of the Dig2 oral appliances can also be predicated by the swellable properties of the hydrogel. In some bleaching embodiments, the prescribed treatment would have the carbamide peroxide contact only the teeth and not the soft tissue of the oral cavity. In some embodiments, if nonswellable hydrogel is used, then Dig2 can subtract from the entire tooth surface about 0.2 mm including from buccal-labial, incisal-occlusal and lingual-palatal. This method would allow the bleaching of the entire tooth surface and not just the outside buccal-labial surface viewed when one smiles and which is the approach virtually all other bleaching systems on the market use today. In yet other embodiments, if a hydrogel is formulated at 50% expansion, then the Dig2 subtraction image would be 50% less to allow for the expansion of the hydrogel to cover the entire tooth. Dig2 could still be 0.2 mm thick but the surface areas of the teeth that are subtracted could be less by 50%. Thus, the physical expansion of the chemical compositions utilized in the oral appliances described herein and the resulting dimensional changes can be manipulated by computer software in a precise scientific manner. For example, to allow further for the swellable properties of hydrogel, the software program can employ a spatial geometric pattern system. In this example, the Dig2 image could print in a geometric or random pattern that accounts for the predetermined expansion of the medicament infused hydrogel. As a result, Dig3, the software program for printing can also take into account the expansion factors of hydrogel when directing the print head to print.

In other embodiments, the swelling properties of the hydrogel can be varied. Multiple print heads of a stereolithography machine can contain different formulations of medicament containing hydrogel which can be employed to treat various conditions at the same time. In one embodiment, one print head can deliver nonswellable hydrogel containing dental bleach while another print head can deliver swellable hydrogel containing medicaments used to manufacture the oral appliance to treat gum disease.

In other embodiments, the Dig3 oral appliance can be utilized as a diagnostic tool for testing of fluids in the oral cavity. In these embodiments, the hydrogel of the Dig3 oral appliance is absorptive both on its internal and external surfaces and can therefore be easily used to test the gingival crevicular fluids and/or saliva present in the oral cavity for diagnostic purposes. After the patient wears the Dig3 oral appliance, the oral appliance can be removed, placed into a container and then sent to a lab for analysis. The Dig3 oral appliance can test oral fluids to do so over longer periods of time and is thus significantly more effective than the fluid spot testing currently used in the prior art. In some embodiments, in place of or in addition to the medicament, the oral appliance can comprise absorptive material that can retain the sample (e.g., cells, fluid (e.g., blood saliva), etc.), such material includes, but is not limited to, absorptive hydrogels, absorptive sponge, or sponge-like material, polyvinyl acetate (PVA), polyurethane (PU), cellulose, polyester, rayon, cotton or a combination thereof.

The dimensions of the oral appliance, among other things, will depend on the target treatment site and whether local or systemic delivery of the medicament is required. The oral appliance can be adapted to any size and shape to receive at least a portion of the teeth and/or soft tissue areas inside the mouth to deliver the medicament. For example, the oral appliance is designed to contour, support and hold the polymer gel material and, in various embodiments, extends to at least the muco-gingival junction, or at least 2 mm to 5 mm buccally or lingually beyond a gingival margin, or contact all or substantially all of one or more teeth and/or soft tissue areas inside the mouth and adjacent buccal and lingual soft tissue areas.

In various embodiments, the oral appliance has a thickness of from about 0.06 inches to about 0.2 inches, a depth of at least about 1 mm to about 5 mm and a width of from about 1 mm to about 10 mm. In certain embodiments, the thickness of surface of the oral appliance is incrementally configured for treatment of a gum disease.

Material of Oral Appliance

The material of the oral appliance can be any material that can hold and release the medicament or in some embodiments, retain a sample (e.g., blood, saliva, cells, etc.). In various embodiments, the material from which the oral appliance can be manufactured includes swellable polymer materials, such as, for example gels, hydrogels, polymer brushes or combinations thereof.

In various embodiments, polymer gels, hydrogels, and brush polymers can be formulated to have varying degrees of swelling ability. Thus, a treatment that involves the application of pressure to soft tissues of the mouth can be accommodated through the specific formulation of Dig2 materials to incorporate the desired amount or percentage of swelling during treatment. In some embodiments, the polymer comprises 20 wt % to 90 wt % of the formulation.

In various embodiments, the molecular weight of the gel can be varied as desired. The choice of method to vary molecular weight is typically determined by the composition of the gel (e.g., polymer, versus non-polymer). For example in various embodiments, when the gel comprises one or more polymers, the degree of polymerization can be controlled by varying the amount of polymer initiators (e.g. benzoyl peroxide), organic solvents or activator (e.g. DMPT), crosslinking agents, polymerization agent, incorporation of chain transfer or chain capping agents and/or reaction time.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel that includes a high molecular weight polymer tends to coagulate or solidify more quickly than a polymeric composition that includes a low-molecular weight polymer. Polymeric gel formulations that include high molecular weight polymers also tend to have a higher solution viscosity than a polymeric gel that includes low-molecular weight polymers. In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000 g/mol.

In various embodiments, the gel has an inherent viscosity (abbreviated as "I.V." and units are in deciliters/gram), which is a measure of the gel's molecular weight and degradation time (e.g., a gel with a high inherent viscosity has a higher molecular weight and may have a longer degradation time). Typically, when the polymers have similar components but different molecular weights, a gel with a high molecular weight provides a stronger matrix and the matrix takes more time to degrade. In contrast, a gel with a low molecular weight degrades more quickly and provides a softer matrix. In various embodiments, the gel has a molecular weight, as shown by the inherent viscosity, from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, and about 1.8 to about 2.1 dL/g.

In some embodiments, when the polymer materials have different chemistries (e.g., high MW DLG 5050 and low MW DL), the high MW polymer may degrade faster than the low MW polymer.

In various embodiments, the gel can have a viscosity of about 300 to about 5,000 centipoise (cp). In other embodiments, the gel can have a viscosity of from about 5 to about 300 cps, from about 10 cps to about 50 cps, or from about 15 cps to about 75 cps at room temperature. The gel may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethylmethacrylate), poly-(methoxyethylmethacrylate), poly(methoxyethoxyethyl methacrylate), polymethylmethacrylate (PMMA), methylmethacrylate (MMA), gelatin, polyvinyl alcohols, propylene glycol, mPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In various embodiments, the gel is a hydrogel made of high molecular weight biocompatible elastomeric polymers of synthetic or natural origin. In other embodiments, the hydrogel material can hold some or all of the liquid medicament when the hydrogel material is hypo-saturated, saturated, or supersaturated with liquid medicament. There are many advantages resulting from using hydrogel in making the oral appliances described herein. Generally, hydrogel materials provide an effective contact medium for gum compression and for holding and diffusion of the medicament selected for treatment. The above can hold the sample (e.g., saliva, blood, cells, etc.) when the oral appliance is removed and then the oral appliance can be sent to the lab for testing.

Hydrogels obtained from natural sources are particularly appealing because they are more likely to be biocompatible for in vivo applications. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly(acrylonitrile-acrylic acid), polyurethanes, polyethylene glycol (for example, PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane, or a combination thereof.

In various embodiments, rather than directly admixing the therapeutic agent into the gel, microspheres may be dispersed within the gel, the microspheres being loaded with medicament. In one embodiment, the microspheres provide for a sustained release of the medicament. In yet another embodiment, the gel, which is biodegradable, prevents the microspheres from releasing the medicament; the microspheres thus do not release the medicament until they have been released from the gel. Dispersed within the gel may be a plurality of microspheres that encapsulate the desired therapeutic agent. Certain of these microspheres degrade once released from the gel, thus releasing the medicament.

Microspheres, much like a fluid, may disperse relatively quickly, depending upon the surrounding tissue type in the oral cavity, and hence disperse the medicament. In some situations, this may be desirable while in others, it may be more desirable to keep the medicament tightly constrained to a well-defined target site.

In various embodiments, also useful material for preparing the oral appliances described in this disclosure comprise reactive segmented block copolymers containing hydrophilic domain(s) and showing good surface properties when the block copolymer is covalently bound to substrates containing complimentary functionality. The hydrophilic domain(s) will comprise at least one hydrophilic monomer, such as, HEMA, glyceryl methacrylate, methacrylic acid ("MAA"), acrylic acid ("AA"), methacrylamide, acrylamide, N,N'-dimethylmethacrylamide, or N,N'-dimethylacrylamide; copolymers thereof; hydrophilic prepolymers, such as ethylenically unsaturated poly(alkylene oxide)s, cyclic lactams such as N-vinyl-2-pyrrolidone ("NVP"), or derivatives thereof. Still further examples are the hydrophilic vinyl carbonate or vinyl carbamate monomers. Hydrophilic monomers can be nonionic monomers, such as 2-hydroxyethyl methacrylate ("HEMA"), 2-hydroxyethyl acrylate ("HEA"), 2-(2-ethoxyethoxy)ethyl(meth)acrylate, glyceryl(meth)acrylate, poly(ethylene glycol(meth)acrylate), tetrahydrofurfuryl(meth)acrylate, (meth)acrylamide, N,N'-dimethylmethacrylamide, N,N'-dimethylacrylamide("DMA"), N-vinyl-2-pyrrolidone (or other N-vinyl lactams), N-vinyl acetamide, and combinations thereof. Still further examples of hydrophilic monomers are the vinyl carbonate and vinyl carbamate monomers disclosed in U.S. Pat. No. 5,070,215, and the hydrophilic oxazolone monomers disclosed in U.S. Pat. No. 4,910,277. The contents of these patents are incorporated herein by reference. The hydrophilic monomer also can be an anionic monomer, such as 2-methacryloyloxyethylsulfonate salts. Substituted anionic hydrophilic monomers, such as from acrylic and methacrylic acid, can also be utilized wherein the substituted group can be removed by a facile chemical process.

The polymer gel material can comprise orally soluble or insoluble polymers. For example, the polymer gel material may be designed to be insoluble in the oral environment, yet still release the medicament that is coated on or internally imbedded in the polymer gel material. Alternatively, the polymer gel material could be designed such that the polymer and one or more medicaments could dissolve in the oral environment. Such orally dissolvable polymer gel material would release imbedded medicaments as the polymer is dissolved away by the flow of saliva. Various polymers whether soluble, insoluble, semi-soluble or combinations of these may be used to create a polymer gel material with specific active ingredient releasing capabilities. Many plastics and plastic combinations are suitable for this application. A few examples of possible plastics include: polyacrylates, polyamide-imide, phenolic, nylon, nitrile resins, petroleum resins, fluoropolymers, copolyvidones (copovidones), epoxy, melamine-formaldehyde, diallyl phthalate, acetal, coumarone-indene, acrylics, acrylonitrile-butadiene-styrene, alkyds, cellulosics, polybutylene, polycarbonate, polycaprolactones, polyethylene, polyimides, polyphenylene oxide, polypropylene, polystyrene, polyurethanes, polyvinyl acetates, polyvinyl chloride, poly(vinyl alcohol-co ethylene), styrene acrylonitrile, sulfone polymers, saturated or unsaturated polyesters, urea-formaldehyde, or any like plastics.

In one embodiment the hydrogel material may comprise a backing material (e.g., a closed cell plastic backing material) to minimize elution of the medicament from the oral appliance, into the oral cavity to minimize ingestion by the patient and/or irritation of the oral cavity tissues. The hyrogels material can be constructed to increase release of the medicament to give a bolus dose or the polymer gel material may be designed to prevent medicament from spilling out of the hydrogel material and allow the medicament to pass through the polymer gel hydrogel over time to obtain a sustained release profile. In other words, in various embodiments, the hydrogel material may have an internal structural spacing sized relative to the viscosity of the medicament to absorb and allow the composition to pass therethrough to achieve the desired medicament release profile, for example, immediate release, bolus release, sustained or controlled release.

The dimensions of the polymer material (e.g., gel, hydrogel, etc.), among other things, will depend on the target treatment site and whether local or systemic delivery of the medicament is required as well as the type of medicament release profile to achieve. The oral appliance prepared is prepared primarily of polymer material and can be adapted to any size and shape required to receive at least a portion of the teeth and/or soft tissue areas inside the mouth to deliver the medicament. For example, the polymer material may, in various embodiments, extend to at least the mucogingival junction, or at least 2 mm to 5 mm buccally or lingually beyond a gingival margin, or contact all or substantially all of one or more teeth and/or soft tissue areas inside the mouth and adjacent buccal and lingual soft tissue areas. In various embodiments, the polymer material contacts all or substantially all of one or more teeth and/or soft tissue areas inside the mouth. In various embodiments, the polymer material contacts the soft tissue and teeth at or near a gingival margin or sulcus. In various embodiments, the polymer material has a thickness of from about 0.06 inches to about 0.2 inches, a depth of at least about 1 mm to about 5 mm and a width of from about 1 mm to about 10 mm.

Medicaments

The polymer material contains one or more medicaments coated, layered on it, impregnated within it at the same or different areas to form a monolithic oral appliance. In various embodiments, some areas of the polymer material do not contain one or more medicaments, and the polymer material may function to hold or lock a portion of the polymer material (e.g., gel, hydrogel, etc.) in place so that other portions of the polymer material can contact the appropriate target site. Thus, in some embodiments, the polymer material may contain one or more medicaments disposed in or on it throughout the whole polymer material. In other embodiments, one or more portions of the polymer material do not contain any medicament disposed in or on it. The term "medicament" as used herein is generally meant to refer to any substance that alters the physiology of a patient. The term "medicament" may be used interchangeably herein with the terms "drug" "therapeutic agent", "therapeutically effective amount", or "active pharmaceutical ingredient". It will be understood that a "medicament formulation" may include more than one therapeutic agent, wherein exemplary combinations of therapeutic agents include a combination of two or more medicaments. The medicament can also include cells, where the device (e.g., oral appliance) can be seeded with the cells, for example, gingival cells or gingival tissue, bone cells, cartilage cells, bone tissue, cartilage tissue so that the device can repair or replace tissue in the treatment area.

The medicament may be in powder, liquid, solid, solution, or suspension (e.g., gel) form and disposed on or impregnated in the polymer material. This may occur during manufacture of the polymer material or it may occur after the polymer material is made. For example, on the core polymer material, the medicament may be layered by solution or suspension layering or powder layering techniques. In solution or suspension layering, the medicament and any inactive ingredients (excipients, binders, etc.) are suspended or dissolved in water or an organic solvent. The resulting liquid is sprayed onto the outside of polymer material to make the polymer material have the desired potency. Solution or suspension layering may be conducted using a wide variety of process techniques, for example, by fluidized bed, Wurster bottom spray techniques, or the like. When the desired potency has been achieved, the polymer material is dried to the desired residual moisture content. Powdered layering involves the application of a dry powder to the polymer material. The powder may contain the drug, or may include excipients such as a binder, flow aid, inert filler, or the like. In the powder layering technique a pharmaceutically acceptable liquid, which may be water, organic solvent, with or without a binder and/or excipients, is applied to the polymer material while applying the dry powder until the desired potency is achieved. When the desired potency has been achieved, the polymer material may be dried to the desired moisture content.

In various embodiments, the medicament may be encapsulated in a lipid bilayer and then impregnated, coated or layered on or into the polymer material. In various embodiments, the medicament can be micro-encapsulated into a carrier having a positive or negative charge, such as for example, a Novasome® (available from IGI) to increase absorption of the medicament or cause it to have sustain release properties to release the medicament over hours (e.g., 1-24 hours or longer). The Novasome® can be made using amphiphiles, which include a variety of fatty alcohols and acids to give the medicament the desired charged and release property. It will be understood that other ionically charged materials can be used as well.

In various embodiments, medicaments can now be used at lower doses as the polymer material improves contact with the target treatment area(s) of the teeth and/or soft tissue. Thus, less dose of the medicament can be used because more effective concentration of medicament at the one or more target sites is achieved over time.

Examples of medicaments include, but are not limited to, anti-inflammatory agents, anti-infective agents (e.g., antiviral, antibacterial, antifungal agents, etc.), tissue and bone growth factors, pain management medication (e.g., analgesics, anesthetics, etc.) antineoplastic agents, tooth whitening agents, breath fresheners, anticalculus agents, antineoplastic agents, oral dermatologics, selective H-2 antagonists, anticaries agents, nutrients, vitamins, minerals, herbal products, or mixtures thereof.

The medicament may be a systemic medicament such as thyroid drug, e.g., anti-thyroid agents or thyrostatic substances that are compounds useful for the treatment of thyroid diseases, including hormones such as thyroxine (T4), triiodothyronine (T3); propylthiouracil; methimazole; and so forth.

In various embodiments, the polymer material may contain more than one medicament. However, in another embodiment, combination therapy will involve use of a single safe and effective amount of the medicament. For example the method may further comprise subsequently administering one or more additional oral appliances, each containing a medicament that is different from the medicament contained in the earlier oral appliance. In this way, a series of customized treatment regimens can be provided to the patient. This provides for a "mix and match" medicament regimen with dose adjustment capability and provides the added advantage of allowing the health professional complete control to administer only those medicaments at the desired strength believed to be appropriate for the disease or condition being treated.

The amount of medicament contained within the polymer material, will vary widely depending on the effective dosage required and rate of release from the polymer material and the length of the desired delivery interval. The dosage administered to the patient can be single or multiple doses and will vary depending upon a variety of factors, including the agent's pharmacokinetic properties, patient conditions and characteristics (sex, age, body weight, health, size, etc.), extent of symptoms, concurrent treatments, frequency of treatment and the effect desired.

In various embodiments, the polymer material is designed to release the medicament as a bolus dose of the medicament, a single dose of the medicament, or multiple doses of the medicament all preloaded with a specific dosage at the manufacturing facility.

Anti-inflammatory agents are of particular interest as it is believed that they serve not only to reduce inflammation but, in doing so, can also have a variety of other beneficial effects that may eliminate the need for or minimize the amount of additional medicaments. For example, if a patient is suffering from pain and inflammation, administration of an anti-inflammatory agent will alleviate inflammation and the tissue, once back to normal may no longer exert pressure on nerves and thus the need for additional pain medication may be minimized or eliminated entirely.

Suitable anti-inflammatory agents to treat and/or reduce inflammation include steroidal and/or non-steroidal anti-inflammatories. Exemplary anti-inflammatory agents include by way of example and not limitation, alclofenac; alclometasone dipropionate; algestone acetonide; alendronate sodium; alpha amylase; amcinafal; amcinafide; amcinonide; amfenac sodium; amiprilose hydrochloride; anakinra; anirolac; anitrazafen; apazone; balsalazide disodium; beclomethasone diproprionate; bendazac; benoxaprofen; benzydamine hydrochloride; betamethasone; bromelains; broperamole; budesonide; carprofen; ciclopeofen; cintazone; cliprofen; clobetasol propionate; clobetasone butyrate; clopirac; cloticasone propionate; cormethasone acetate; cortisone acetate; cortodoxone; deflazacort; desonide; desoximetasone; dexamethasone dipropionate; diclofenac potassium; diclofenac sodium; diflorasone diacetate; diflumidone sodium; diflunisal; difluprednate; diftalone; dimethyl sulfoxide; drocinonide; endrysone; enlimomab; enolicam sodium; epirizole; etodolac; etofenamate; felbinac; fenamole; fenbufen; fenclofenac; fenclorac; fendosal; fenpipalone; fentiazac; flazalone; fluazacort; fludrocortisone; flufenamic acid; flumizole; flunisolide acetate; flunixin; flunixin meglumine; fluocinonide; fluocinolone acetonide; fluocortin butyl; fluorometholone acetate; fluquazone; flurandrenolide; flurbiprofen; fluretofen; fluticasone propionate; furaprofen; furobufen; halcinonide; halobetasol propionate; halopredone acetate; hydrocortisone; ibufenac; ibuprofen; ibuprofen aluminum; ibuprofen piconol; ilonidap; indomethacin; indomethacin sodium; indoprofen; indoxole; intrazole; isoflupredone acetate; isoxepac; isoxicam; ketoprofen; lofemizole hydrochloride; lomoxicam; loteprednol etabonate; meclofenamate sodium; meclofenamic acid; meclorisone dibutyrate; medrysone; mefenamic acid; mesalamine; meseclazone; methylprednisolone suleptanate; momiflumate; nabumetone; naproxen; naproxen sodium; naproxol; nimazone; nilutamide; olsalazine sodium; orgotein; orpanoxin; oxaprozin; oxyphenbutazone; pamidronate disodium; paramethasone; paranyline hydrochloride; pentosan polysulfate sodium; phenbutazone sodium glycerate; pirfenidone; piroxicam; piroxicam cinnamate; piroxicam olamine; pirprofen; prednazate; prednisolone; prifelone; prodolic acid; proquazone; proxazole; proxazole citrate; rimexolone; romazarit; salcolex; salnacedin; salsalate; sanguinarium chloride; seclazone; sermetacin; sudoxicam; sulindac; suprofen; talmetacin; talniflumate; talosalate; tebufelone; tenidap; tenidap sodium; tenoxicam; tesicam; tesimide; tetrydamine; tiopinac; tixocortol pivalate; tolmetin; tolmetin sodium; triamcinelone; triclonide; triflumidate; zidometacin; zomepirac sodium or combinations thereof.

Anti-inflammatory agents include steroidal agents or glucocorticosteroids. Phospholipase A2 ("PLA2") is a lipolytic enzyme that has been implicated as a possible mediator of inflammation. Specifically, PLA2 hydrolyses the 2-acyl position of glycerophospholipids, liberating free-fatty acids, mainly arachidonic acid. Subsequently, it is believed that arachidonic acid is converted into a variety of proinflammatory eicosanoids. Glucocorticosteroids are known to stop or reduce the suggested mechanisms of inflammation that involves the activation of the arachidonic acid cascade, which results in the liberation of a variety of proinflammatory eicosanoids by inducing lipocortin that inhibits PLA2. This provides a significant advantage over non-steroidal anti-inflammatory agents that enter the cascade much later.

Suitable glucocorticosteroids include, but are not limited to, alclometasone diproprionate, alendronate sodium, amcinonide, beclomethasone diproprionate, betamethasone, budesonide, clobetasol propionate, cortisone, dexamethasone, diflorasone diacetate, hydrocortisone, fludrocortisone; flunisolide acetate, fluocinolone acetonide, fluocinonide, fluorometholone acetate, flurandrenolide, halcinonide, medrysone; methylprednisone suleptanate, pamidronate, paramethasone, prednisolone, nilutamide, triamcinelone, or combinations thereof.

Dexamethasone is of particular interest for use as an anti-inflammatory to treat orofacial diseases. Besides its anti-inflammatory property, dexamethasone can be delivered to up-regulate certain enzyme activities. Specifically dexamethasone can be used to increase or up-regulate alkaline phosphotase activity in regenerating human periodontal cells.

Exemplary anti-infective agents to treat infection include by way of example and not limitation, antibacterial agents; quinolones and in particular fluoroquinolones (e.g., norfloxacin, ciprofloxacin, lomefloxacin, ofloxacin, etc.), aminoglycosides (e.g., gentamicin, tobramycin, etc.), glycopeptides (e.g., vancomycin, etc.), lincosamides (e.g., clindamycin), cephalosporins (e.g., first, second, third generation) and related beta-lactams, macrolides (e.g., azithromycin, erythromycin, etc.), nitroimidazoles (e.g., metronidazole), penicillins, polymyxins, tetracyclines, or combinations thereof.

Other exemplary antibacterial agents include, by way of illustration and not limitation, acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; cefranide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; ganciclovir and ganciclovir sodium; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin and oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillins such as penicillin g benzathine, penicillin g potassium, penicillin g procaine, penicillin g sodium, penicillin v, penicillin v benzathine, penicillin v hydrabamine, and penicillin v potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; ro saramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin dis odium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; zorbamycin; or combinations thereof.

Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperi sone, tubocuarine, vecuronium, and combinations thereof. Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

Exemplary analgesics include, but are not limited to, acetaminophen; alfentanil hydrochloride; aminobenzoate potassium; aminobenzoate sodium; anidoxime; anileridine; anileridine hydrochloride; anilopam hydrochloride; anirolac; antipyrine; aspirin; benoxaprofen; benzydamine hydrochloride; bicifadine hydrochloride; brifentanil hydrochloride; bromadoline maleate; bromfenac sodium; buprenorphine hydrochloride; butacetin; butixirate; butorphanol; butorphanol tartrate; carbamazepine; carbaspirin calcium; carbiphene hydrochloride; carfentanil citrate; ciprefadol succinate; ciramadol; ciramadol hydrochloride; clonixeril; clonixin; codeine; codeine phosphate; codeine sulfate; conorphone hydrochloride; cyclazocine; dexoxadrol hydrochloride; dexpemedolac; dezocine; diflunisal; dihydrocodeine bitartrate; dimefadane; dipyrone; doxpicomine hydrochloride; drinidene; enadoline hydrochloride; epirizole; ergotamine tartrate; ethoxazene hydrochloride; etofenamate; eugenol; fenoprofen; fenoprofen calcium; fentanyl citrate; floctafenine; flufenisal; flunixin; flunixin meglumine; flupirtine maleate; fluproquazone; fluradoline hydrochloride; flurbiprofen; hydromorphone hydrochloride; ibufenac; indoprofen; ketazocine; ketorfanol; ketorolac and ketorolac tromethamine; letimide hydrochloride; levomethadyl acetate; levomethadyl acetate hydrochloride; levonantradol hydrochloride; levorphanol tartrate; lofemizole hydrochloride; lofentanil oxalate; lorcinadol; lomoxicam; magnesium salicylate; mefenamic acid; menabitan hydrochloride; meperidine hydrochloride; meptazinol hydrochloride; methadone hydrochloride; methadyl acetate; methopholine; methotrimeprazine; metkephamid acetate; mimbane hydrochloride; mirfentanil hydrochloride; molinazone; morphine sulfate; moxazocine; nabitan hydrochloride; nalbuphine hydrochloride; nalmexone hydrochloride; namoxyrate; nantradol hydrochloride; naproxen; naproxen sodium; naproxol; nefopam hydrochloride; nexeridine hydrochloride; noracymethadol hydrochloride; ocfentanil hydrochloride; octazamide; olvanil; oxetorone fumarate; oxycodone; oxycodone hydrochloride; oxycodone terephthalate; oxymorphone hydrochloride; pemedolac; pentamorphone; pentazocine; pentazocine hydrochloride; pentazocine lactate; phenazopyridine hydrochloride; phenyramidol hydrochloride; picenadol hydrochloride; pinadoline; pirfenidone; piroxicam olamine; pravadoline maleate; prodilidine hydrochloride; profadol hydrochloride; propiram fumarate; propoxyphene hydrochloride; propoxyphene napsylate; proxazole; proxazole citrate; proxorphan tartrate; pyrroliphene hydrochloride; remifentanil hydrochloride; salcolex; salethamide maleate; salicylamide; salicylate meglumine; salsalate; sodium salicylate; spiradoline mesylate; sufentanil; sufentanil citrate; talmetacin; talniflumate; talosalate; tazadolene succinate; tebufelone; tetrydamine; tifurac sodium; tilidine hydrochloride; tiopinac; tonazocine mesylate; tramadol hydrochloride; trefentanil hydrochloride; trolamine; veradoline hydrochloride; verilopam hydrochloride; volazocine; xorphanol mesylate; xylazine hydrochloride; zenazocine mesylate; zomepirac sodium; zucapsaicin or combinations thereof.

Exemplary anesthetics include by way of example and not limitation, alflurane; benoxinate hydrochloride; benzocaine; biphenamine hydrochloride; bupivacaine hydrochloride; butamben; butamben picrate; chloroprocaine hydrochloride; cocaine; cocaine hydrochloride; cyclopropane; desflurane; dexivacaine; diamocaine cyclamate; dibucaine; dibucaine hydrochloride; dyclonine hydrochloride; enflurane; ether; ethyl chloride; etidocaine; etoxadrol hydrochloride; euprocin hydrochloride; fluroxene; halothane; isobutamben; isoflurane; ketamine hydrochloride; levoxadrol hydrochloride; lidocaine; lidocaine hydrochloride; mepivacaine hydrochloride; methohexital sodium; methoxyflurane; midazolam hydrochloride; midazolam maleate; minaxolone; nitrous oxide; norflurane; octodrine; oxethazaine; phencyclidine hydrochloride; pramoxine hydrochloride; prilocaine hydrochloride; procaine hydrochloride; propanidid; proparacaine hydrochloride; propofol; propoxycaine hydrochloride; pyrrocaine; risocaine; rodocaine; roflurane; salicyl alcohol; sevoflurane; teflurane; tetracaine; tetracaine hydrochloride; thiamylal; thiamylal sodium; thiopental sodium; tiletamine hydrochloride; zolamine hydrochloride; or combinations thereof.

The polymer material can be saturated with one or more analgesics that can anesthetize the patients tooth and/or soft tissue area before the dental procedure is performed. In this way, the patient can place the oral appliance inside the oral cavity and the pre-filled oral appliance and polymer material will numb the particular site. When the patient visits the dental professional, little delay can occur while waiting for the area to numb. In this way, fast efficient dental procedures (e.g., tooth fillings, tooth extractions, root canal, dental cleanings, etc.) can be performed without delay to the dental provider or patient.

The polymer material may contain one or more antineoplastic agents to treat cancer. Exemplary antineoplastic agents include by way of example and not limitation, acivicin; aclarubicin; acodazole hydrochloride; acrqnine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; ethiodized oil I 131; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; gold Au 198; hydroxyurea; idarubicin hydrochloride; ifosfamide; ilmofosine; interferon alpha-2a; interferon alpha-2b; interferon .alpha n1; interferon alpha n3; interferon beta Ia; interferon gamma Ib; iproplatin; irinotecan hydrochloride; lanreotide acetate; letrozole; leucovorin in combination with fluorouracil or methotrexate; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safmgol; safingol hydrochloride; semustine; simtrazene; sparfosate sodium; sparsomycin; spirogermanium hydrochloride; spiromustine; spiroplatin; streptonigrin; streptozocin; strontium chloride Sr 89; sulofenur; talisomycin; taxane; taxoid; tecogalan sodium; tegafur; teloxantrone hydrochloride; temoporfin; teniposide; teroxirone; testolactone; thiamiprine; thioguanine; thiotepa; tiazofurin; tirapazamine; topotecan hydrochloride; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride; or combinations thereof.

The polymer material may contain one or more oral care medicaments that, in various embodiments, provide a benefit to the patient, without detriment to the oral surface to which it is applied. Examples of the oral conditions these medicaments address include, but, are not limited to, appearance to the teeth, whitening, stain bleaching, stain removal, plaque removal, tartar removal, cavity prevention and treatment, tooth recalcification, oral infections, inflamed and/or bleeding gums, mucosal wounds, lesions, ulcers, aphthous ulcers, cold sores, tooth abscesses, gingivitis, periodontal disease, xerostomia, post-surgical dressings and the elimination of mouth malodor.

For example, the tight fit of the oral appliance further forces the medicament, by its three dimensional form, out of the polymer material to pool at the gingival margin but also causes to compress it and force it into the gingival sulcus and into the periodontal pockets. This is precisely where active periodontal disease is and where the medicament will be delivered. It is also an area with tremendous capillary blood flow and absorption. Thus, if desired, a medicament can be used that can provide systemic treatment, for example, for hypertension medication, diabetes medication, asthma medication.

In some embodiments, the friction, force or scratching from the oral appliance on or in the oral cavity will cause release of the medicament at or near the target site.

Patients undergoing head and neck radiation treatment for cancer often suffer from high incidences of dental caries because of xerostomia (dry mouth). Xerostomia may also be caused by salivary gland disease, various medications and other causes. The oral appliance, in various embodiments, allows the patient to self administer a wide variety of medicaments comfortably, painlessly and in the convenience of their own home.

In various embodiments, suitable medicaments include any material that is generally considered safe for use in the oral cavity and that provides changes to the overall appearance and/or health of the patient. The level of medicament is generally, unless specifically noted, from about 0.01% to about 50% or from about 0.1% to about 20% or from about 0.5% to about 10% or from about 1% to about 7%, by weight of the composition.

The polymer material may comprise a safe and effective amount of one or more whitening agents such as bleaching agents or abrasive agents. Generally the level of the bleaching agent is dependent on the available oxygen or chlorine respectively that the molecule is configured for providing to bleach the stain. The bleaching agent may be present at levels from about 0.1% to about 20%, in another embodiment from about 0.5% to about 9% and in another embodiment from about 3% to about 8%, and in yet another embodiment from about 4% to about 6%, by weight of the bleaching agent composition.

Typical bleaching agents suitable for use in the present application include but are not limited to, peroxides, metal chlorites, perborates, percarbonates, peroxyacids, persulfates, compounds that form the preceding compounds in situ, and combinations thereof. Suitable peroxide compounds include hydrogen peroxide, urea peroxide, calcium peroxide, carbamide peroxide, and mixtures thereof. In one embodiment the bleaching agent is carbamide peroxide. Suitable metal chlorites include calcium chlorite, barium chlorite, magnesium chlorite, lithium chlorite, sodium chlorite, potassium chlorite, and mixtures thereof. Additional bleaching agents also include hypochlorite and chlorine dioxide. In one embodiment the bleaching agent is selected from sodium chlorite, peroxide, sodium percarbonate, oxones, and mixtures thereof. The starting bleach agent can be aqueous or solid material.

The polymer material may comprise a safe and effective amount of an anticaries agent or mixtures thereof. In various embodiments, the anticaries agent can comprise xylitol, a fluoride ion source, and mixtures thereof. The fluoride ion source provides free fluoride ions during the use. Examples of fluoride ion sources include, but are not limited to, sodium fluoride, stannous fluoride, indium fluoride, organic fluorides such as amine fluorides, and sodium monofluorophosphate or combination thereof. In various embodiments, the medicament provides from about 50 ppm to 10,000 ppm or from about 100 to 3000 ppm of fluoride ions that contact tooth surfaces.

In various embodiments, the polymer material may comprise a safe and effective amount of at least one anticalculus agent. This amount is generally from about 0.01% to about 40% by weight of the composition, in another embodiment from about 0.1% to about 25%, and in yet another embodiment from about 4.5% to about 20%, and in yet another embodiment from about 5% to about 15%, by weight of the composition. The anticalculus agent should also be compatible with the other components of the composition.

The anticalculus agent can contain polyphosphates and salts thereof; polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof. In one embodiment, the salts are alkali metal salts. In another embodiment the anticalculus agent is a pyrophosphate, polyphosphate, and mixtures thereof.

In various embodiments, the polymer material may comprise a safe and effective amount of at least one selective H-2 antagonist. Selective H-2 antagonists include, but are not limited to, cimetidine, etintidine, ranitidine, ICIA-5165, tiotidine, ORF-17578, lupitidine, donetidine, famotidine, roxatidine, pifatidine, lamtidine, BL-6548, BMY-25271, zaltidine, nizatidine, mifentidine, BMY-25368 (SKF-94482), BL-6341A, ICI-162846, ramixotidine, Wy-45727, SR-58042, BMY-25405, loxtidine, DA-4634, bisfentidine, sufotidine, ebrotidine, HE-30-256, D-16637, FRG-8813, FRG-8701, impromidine, L-643728, and HB-408, burimamide, metiamide or combination thereof.

In various embodiments, the polymer material may comprise a safe and effective amount of at least one nutrient that may improve the condition of the oral cavity and can be included in the polymer material. Nutrients include minerals, vitamins, oral nutritional supplements, enteral nutritional supplements, and mixtures thereof. Minerals include, but are not limited to, calcium, phosphorus, fluoride, zinc, manganese, potassium and mixtures thereof.

Vitamins can be included with minerals or used separately. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof.

Oral nutritional supplements may also be included in the polymer material. Oral nutritional supplements include amino acids, lipotropics, fish oil, and mixtures thereof. Amino acids include, but are not limited to L-Tryptophan, L-Lysine, Methionine, Threonine, Levocarnitine or L-carnitine and mixtures thereof. Lipotropics include, but, are not limited to choline, inositol, betaine, linoleic acid, linolenic acid, and mixtures thereof. Fish oil contains large amounts of Omega-3 (N-3) polyunsaturated fatty acids, eicosapentaenoic acid and docosahexaenoic acid. Antioxidants may be included such as, for example, Vitamin E, ascorbic acid, Uric acid, carotenoids, Vitamin A, flavonoids and polyphenols, herbal antioxidants, melatonin, aminoindoles, lipoic acids and mixtures thereof.

Enteral nutritional supplements include, but, are not limited to protein products, glucose polymers, corn oil, safflower oil, medium chain triglycerides, flax seed oil. Antipain or desensitizing agents can also be included in or on the polymer material. Such agents may include, but are not limited to, strontium chloride, potassium nitrate, natural herbs such as gall nut, Asarum, Cubebin, Galanga, scutellaria, Liangmianzhen, Baizhi, etc.

The polymer material may contain one or more herbal products that occur in nature or come from plants. Some herbal medicaments include, but are not limited to, chondroitin sulfate, echinacea, ephedra (also called ma huang), garlic, *ginkgo biloba*, ginseng, glucosamine, kava, melatonin, phytoestrogens (such as black cohosh, dong quai and soy), saw palmetto, bee pollen, St. John's wort, or a combination thereof.

Apart from the active medicament, the polymer material may optionally contain bulking agents, disintegrants, binders and lubricants, and excipients, which have no decisive effect on the delivery of active substances. Examples are, alginate, inter alia, bentonite (alumina silica hydrate), silica, cellulose (normally microcrystalline cellulose) or cellulose derivatives, for example methylcellulose, sodium carboxymethylcellulose, sugars such as lactose, starches, for example maize starch or derivatives thereof, for example sodium carboxymethyl-starch, starch paste, phosphoric acid salts, for example di- or tricalcium phosphate, gelatin, stearic acid or suitable salts thereof, for example magnesium stearate or calcium stearate, talc, colloidal silica and similar ancillary substances.

In an exemplary embodiment, a method of delivering a medicament to at least a portion of teeth and/or soft tissue areas inside a mouth is provided, the method comprising: providing an oral appliance comprising an interior surface having a medicament disposed in or on at least a portion of and/or all of the interior surface of the oral appliance, the interior surface being formed to fit contours of at least the portion of the teeth and/or soft tissue areas inside the oral cavity and being configured for supporting and holding the medicament in contact with at least the portion of the teeth and/or soft tissue areas inside the oral cavity to deliver the medicament. In other embodiments, the oral appliance comprises a polymer and at least one medicament.

The oral appliance can be used for treatment of diseases or conditions requiring therapy including whitening teeth. Treating or treatment of a disease refers to executing a protocol, which may include administering one or more oral appliance to a human patient or the patient may self-administer the oral appliance, in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

"Localized" delivery includes delivery where one or more medicaments contact the tooth and/or soft tissue areas, for example, the gingival margin of the mouth or a region of the inside of the mouth, or in close proximity thereto. "Targeted delivery" includes delivery of one or more medicaments at the target site as needed for treatment of the disease or condition including cosmetic applications, for example, whitening teeth or removing stains.

The oral appliance may be transparent, disposable and/or sterilizable. In various embodiments, one or more components of the device are sterilized by radiation in a terminal sterilization step in the final packaging. Terminal sterilization of a product provides greater assurance of sterility than from processes such as an aseptic process, which require individual product components to be sterilized separately and the final package assembled in a sterile environment. Other methods may also be used to sterilize one or more components of the oral appliance, including, but not limited to, E-beam radiation, gamma radiation, gas sterilization, such as, for example, with ethylene oxide or steam sterilization.

The oral appliance may be used for localized and/or targeted delivery of the medicament to a patient to treat a disease or condition. Examples of diseases or conditions include, but, are not limited to, whitening, stain bleaching, stain removal, plaque removal, tartar removal, cavity prevention and treatment, tooth recalcification, oral infections, inflamed and/or bleeding gums, mucosal wounds, lesions, ulcers, aphthous ulcers, cold sores, tooth abscesses, gingivitis, periodontal disease, xerostomia and the elimination of mouth malodor. Some systemic diseases or conditions include, but are not limited to, hypertension, TMJ, migraines, GI ulcers, cardiac conditions, diabetes, neoplastic diseases, oral dermatologic diseases (e.g., lichen planus), hypothyroidism, hyperthyroidism, arthritis, or the like or combinations thereof.

Computer Implemented System

In various embodiments, the present disclosure provides a computer implemented method of making an oral appliance. The method comprises creating a digital record of a patient's oral cavity, the Base Image (BI), by obtaining a digital image of at least a portion of the teeth, and/or soft tissue of the oral cavity by using an imaging device. The Base Image is additively overlayed to create a first digital image, Dig1. Subsequently, a second digital image, Dig2, comprising at least a portion of the teeth and/or soft tissue of the oral cavity in need of treatment is subtractively generated. Thereafter, the first digital image, Dig1, and the second digital image, Dig2, are combined to form a third digital image, Dig3, of the oral cavity treatment area and the third digital image is then stored in the computer and used for manufacture.

In some embodiments, there is a computer implemented method of producing an oral appliance pre-loaded with at least one medicament using a computer, comprising: using the Base Image of the digital image of the patient's mouth, generating first digital data representing an overlay of at least a portion of the teeth and/or soft tissues areas of the oral cavity of a patient, generating second digital data by performing a digital segmentation of at least a portion of the teeth and/or soft tissues areas of the oral cavity to determine discrete regions of the oral cavity in need of treatment, combining the first digital data and the second digital data to form third digital data from which the oral appliance can be produced, wherein the third digital data comprises positions for at least one medicament to be placed at the discrete regions in the oral cavity in need of treatment.

In other embodiments, a computer-implemented method is provided for creating a treatment plan for delivering a medicament to at least a portion of the teeth and/or soft tissue areas inside the oral cavity. The computer-implemented method comprises generating a first digital data, Dig1, representing at least a portion of the teeth and/or soft tissues areas of the oral cavity of a patient from the Base Image. Subsequently, a second digital data, Dig2, is generated by performing via the computer a digital segmentation of at least a portion of the teeth and/or soft tissues areas of the oral cavity comprising discrete regions of the oral cavity in need of treatment. The first digital data, Dig1, and the second digital data, Dig2, are then combined via computer to form the third digital data, Dig3, from which the oral appliance can be produced, wherein the oral appliance has at least one medicament positioned at the discrete regions requiring treatment in the oral cavity.

In various embodiments, a computer based system further comprises creating a virtual 3D image of the oral appliance indicating the discrete regions requiring treatment in the oral cavity; displaying on a display the virtual 3D image and performing interactive treatment plans including the selection of the at least one medicament. Imaging devices utilized to generate the various digital data sets include, without limitations, a digital camera, X-ray device, hand-held 3-D scanner, laser scanner, computerized tomography (CT) scanner, magnetic resonance imaging (MRI) scanner, coordinate measuring machine, destructive scanner or ultrasound scanner, generating first digital data, Dig1, representing at least a portion of the teeth and/or soft tissues areas of the oral cavity of a patient based on an imaging device image (Base Image), generating second digital data, Dig2, by performing via the computer a digital segmentation of at least a portion of the teeth and/or soft tissues areas of the oral cavity comprising discrete regions of the oral cavity in need of treatment, combining via the computer the first digital data, Dig1, and the second digital data, Dig2, to form third digital data, Dig3, from which the oral appliance can be produced having at least one medicament positioned at the discrete regions requiring treatment in the oral cavity In other embodiments, the three-dimensional representation of the third digital data, Dig3, is stored in a format suitable for use by a manufacturer to produce the oral appliance pre-loaded with at least one medicament at areas targeted for treatment. A stereolithography apparatus comprising at least two print heads can be used to manufacture the oral appliances described in this disclosure. As discussed above, the first print head can be configured to deliver a first chemical composition according to the first digital data, Dig1, and the second print head can be configured to deliver a second chemical composition according to the second digital data, Dig2, The two combined merge and represent the image of the third digital data, Dig3. At least one of the chemical compositions includes a medicament while the other can be a polymer gel, hydrogel, brush polymer, another medicament or combinations thereof.

Figure 6:
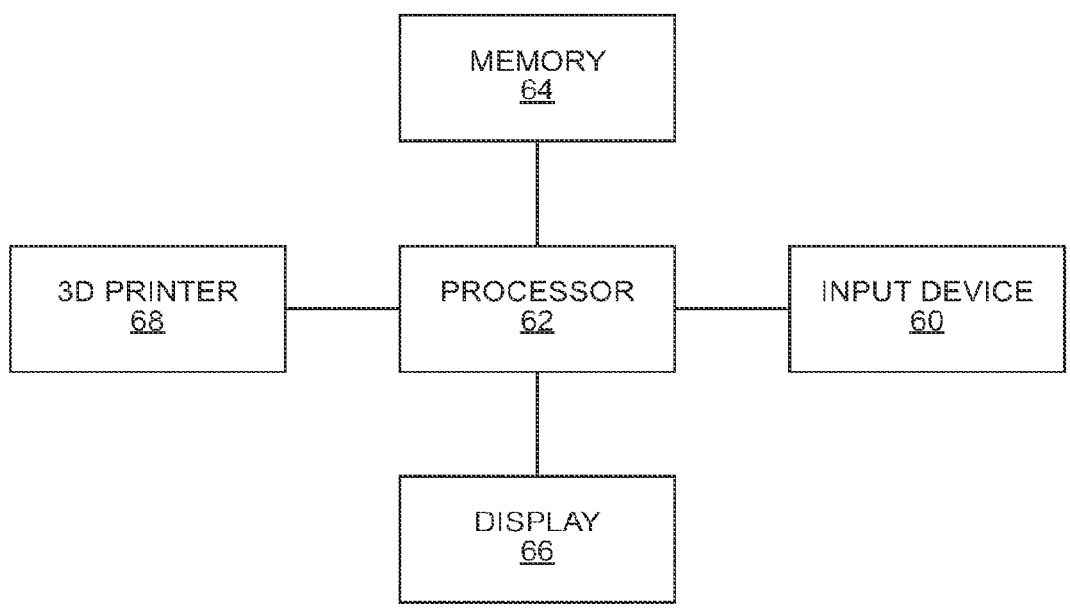
FIG. 6 illustrates an embodiment of the computer-implemented system for producing a pre-loaded oral appliance.

Referring to FIG. 6, it illustrates an embodiment of the computer-implemented system for producing an oral appliance. An input device or scanner 60 is used to scan the oral cavity of and thus generate a digital record of the patient's mouth (BI). The scanner can be an MRI scanner, a CT scanner, a PET scanner, a digital scanner, an X-Ray machine, or an intra-oral scanner, for example. In various embodiments, scanner 60 can scan the patient's teeth, soft tissue, or both to obtain a digital data set of the teeth and/or soft tissue areas inside the mouth from which is generated the Base Image. The digital data can be stored in a database, such as for example a computer that has a processor 62, which sends the digital data to its memory 64 and/or can display it in a virtual 3D image display 66 of processor 62. The database and/or processor can comprise an input device (e.g., keyboard, touch screen, voice activation, etc.) to allow a user to enter, display, edit, and/or transmit on or more images from Dig1, Dig2, Dig3. The processor 62 comprises logic to execute one or more instructions to carry instructions of the computer system (e.g., transmit instructions to the 3D printer, etc.). The logic for executing instructions may be encoded in one or more tangible media for execution by the processor 62. For example, the processor 62 may execute codes stored in a computer-readable medium such as memory 64. The computer-readable medium may be, for example, electronic (e.g., RAM (random access memory), ROM (read-only memory), EPROM (erasable programmable read-only memory)), magnetic, optical (e.g., CD (compact disc), DVD (digital video disc)), electromagnetic, semiconductor technology, or any other suitable medium.

Based on memory 64, processor 62 can generate Dig2 and Dig3 and thereafter send a 3D image to the 3D printer 68 of a stereolithography apparatus.

In various embodiments, an authorized user can input, edit data and approve or prescribe a treatment plan based on the virtual 3D images displayed at the user interface of the computer processor 62 and/or another treating computer networked with computer processor 62. Although the components of the system of FIG. 6 are shown as separate, they may combined in one or more computer systems. Indeed, they may be one or more hardware, software, or hybrid components residing in (or distributed among) one or more local or remote computer systems. It also should be readily apparent that the components of the system as described herein may be merely logical constructs or routines that are implemented as physical components combined or further separated into a variety of different components, sharing different resources (including processing units, memory, clock devices, software routines, logic commands, etc.) as required for the particular implementation of the embodiments disclosed. Indeed, even a single general purpose computer (or other processor-controlled device) executing a program stored on an article of manufacture (e.g., recording medium or other memory units) to produce the functionality referred to herein may be utilized to implement the illustrated embodiments. It also will be understood that the a plurality of computers or servers can be used to allow the system to be a network based system having a plurality of computers linked to each other over the network or Internet or the plurality of computers can be connected to each other to transmit, edit, and receive data via cloud computers.

The computer (e.g., memory, processor, storage component, etc.) may be accessed by authorized users. Authorized users may include at least one dentist or dental specialist, dental hygienist, oral surgeon, physician, surgeon, nurse, patient, and/or health care provider, manufacturer, etc.).

The user can interface with the computer via a user interface that may include one or more display devices (e.g., CRT, LCD, or other known displays) or other output devices (e.g., printer, etc.), and one or more input devices (e.g., keyboard, mouse, stylus, touch screen interface, or other known input mechanisms) for facilitating interaction of a user with the system via user interface. The user interface may be directly coupled to database or directly coupled to a network server system via the Internet or cloud computing. In accordance with one embodiment, one or more user interfaces are provided as part of (or in conjunction with) the illustrated systems to permit users to interact with the systems.

The user interface device may be implemented as a graphical user interface (GUI) containing a display or the like, or may be a link to other user input/output devices known in the art. Individual ones of a plurality of devices (e.g., network/stand-alone computers, personal digital assistants (PDAs), WebTV (or other Internet-only) terminals, set-top boxes, cellular/phones, screenphones, pagers, blackberry, smart phones, iPhone, iPad, table, peer/non-peer technologies, kiosks, or other known (wired or wireless) communication devices, etc.) may similarly be used to execute one or more computer programs (e.g., universal Internet browser programs, dedicated interface programs, etc.) to allow users to interface with the systems in the manner described. Database hardware and software can be developed for access by users through personal computers, mainframes, and other processor-based devices. Users may access and data stored locally on hard drives, CD-ROMs, stored on network storage devices through a local area network, or stored on remote database systems through one or more disparate network paths (e.g., the Internet).

The database can be stored in storage devices or systems (e.g., Random Access Memory (RAM), Read Only Memory (ROM), hard disk drive (HDD), floppy drive, zip drive, compact disk-ROM, DVD, bubble memory, flash drive, redundant array of independent disks (RAID), network accessible storage (NAS) systems, storage area network (SAN) systems, etc.), CAS (content addressed storage) may also be one or more memory devices embedded within a CPU, or shared with one or more of the other components, and may be deployed locally or remotely relative to one or more components interacting with the memory or one or more modules. The database may include data storage device, a collection component for collecting information from users or other computers into centralized database, a tracking component for tracking information received and entered, a search component to search information in the database or other databases, a receiving component to receive a specific query from a user interface, and an accessing component to access centralized database. Receiving component is programmed for receiving a specific query from one of a plurality of users. The database may also include a processing component for searching and processing received queries against data storage device containing a variety of information collected by collection device.

The disclosed system may, in some embodiments, be a computer network based system. The computer network may take any wired/wireless form of known connective technology (e.g., corporate or individual LAN, enterprise WAN, intranet, Internet, Virtual Private Network (VPN), combinations of network systems, etc.) to allow a server to provide local/remote information and control data to/from other locations (e.g., other remote database servers, remote databases, network servers/user interfaces, etc.). In accordance with one embodiment, a network server may be serving one or more users over a collection of remote and disparate networks (e.g., Internet, intranet, VPN, cable, special high-speed ISDN lines, etc.). The network may comprise one or more interfaces (e.g., cards, adapters, ports) for receiving data, transmitting data to other network devices, and forwarding received data to internal components of the system (e.g., 3D printers, printer heads, etc.).

In accordance with one embodiment of the present application, the data may be downloaded in one or more textual/graphical formats (e.g., RTF, PDF, TIFF, JPEG, STL, XML, XDFL, TXT etc.), or set for alternative delivery to one or more specified locations (e.g., via e-mail, fax, regular mail, courier, etc.) in any desired format (e.g., print, storage on electronic media and/or computer readable storage media such as CD-ROM, etc.). The user may view viewing the search results and underlying documents at the user interface, which allows viewing of one or more documents on the same display.

In various embodiments, the computer software can create a 2D or 3D digital image of the patient's oral cavity to allow the treatment provider to review and discuss the proposed treatment with the patient. In another embodiment, the software can process the scanned data and provide the user/operator with useful data including tooth measurements (e.g. arch width, arch length, tooth size, angulations, sulcus size, etc.) to assist the user in fine-tuning the treatment plan. The computer can then provide the operator with options in staging the treatment plan from one stage to another stage, or it can completely generate all stages ranging from the initial to final desired stage. The staging can be done automatically.

Figure 7:
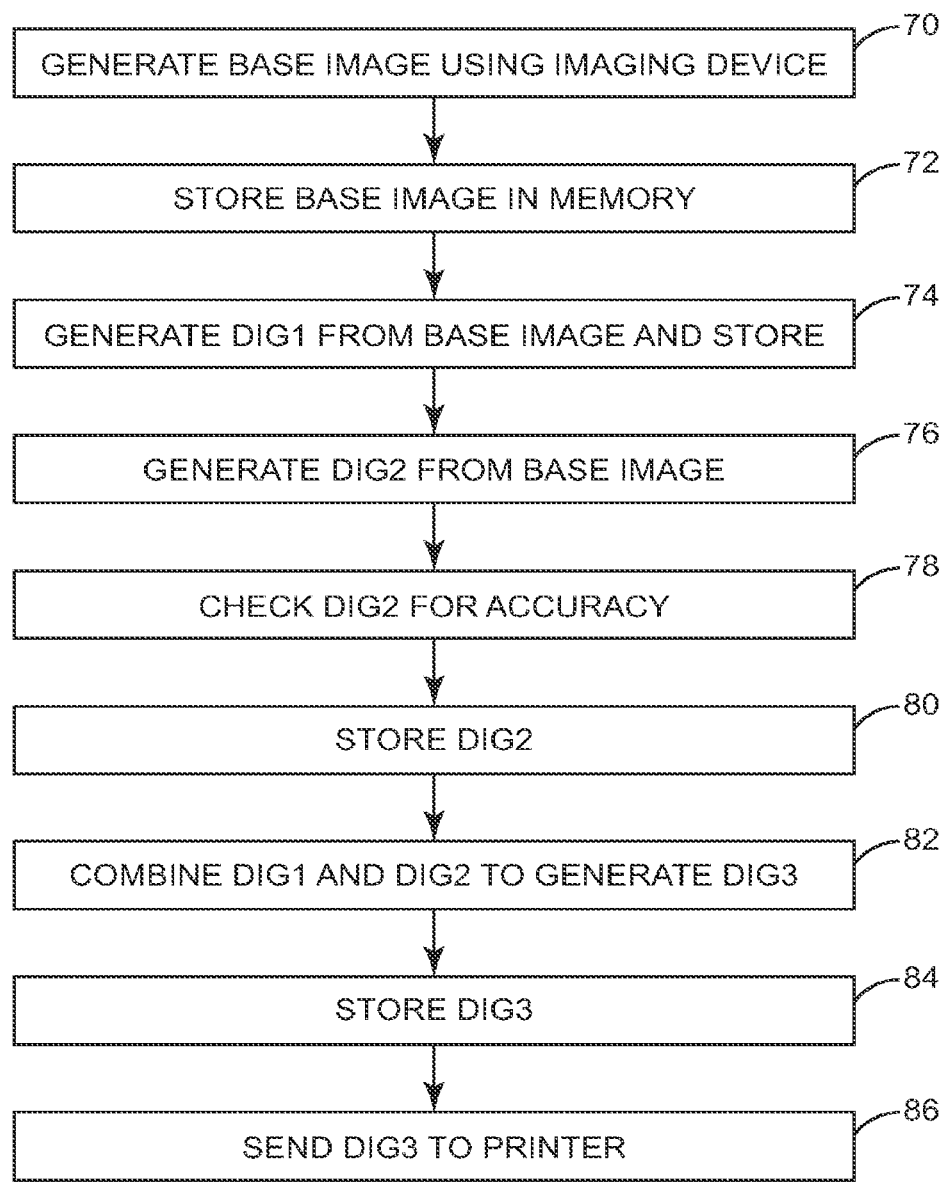
FIG. 7 is a flow chart illustrating an embodiment of the computer-implemented system for producing a pre-loaded oral appliance.

FIG. 7 is a flow chart illustrating the logic steps followed by processor 62. The first step 70 comprises generating a Base Image (BI) of at least a portion of the teeth and/or soft tissues by using an imaging device. In step 72, the BI is stored in the memory of the processor. In step 74, a first data set (Dig1) is generated by the computer additively layering over the BI of at least a portion of the teeth and/or soft tissues. The Dig1 is stored.

In step 76, a second data set (Dig2) is generated by digitally segmenting at least a portion of the teeth and/or soft tissues from the Base Image.

Thereafter, in step 78, the processor can decide if all discrete regions of the oral cavity in need of treatment have been identified or if they have not been, then the digital segmentation step will occur again. Dig2 will also be checked for accuracy.

If all the desired discrete regions have been identified, then in step 80, the processor stores the data, which includes the discrete regions in need of treatment as a separate set corresponding to Dig2. The first and second data sets are combined in step 82 to generate a third data set corresponding to Dig3. The third data set is stored in step 84 and then sent to a 3D printer in step 86.

Figure 8:
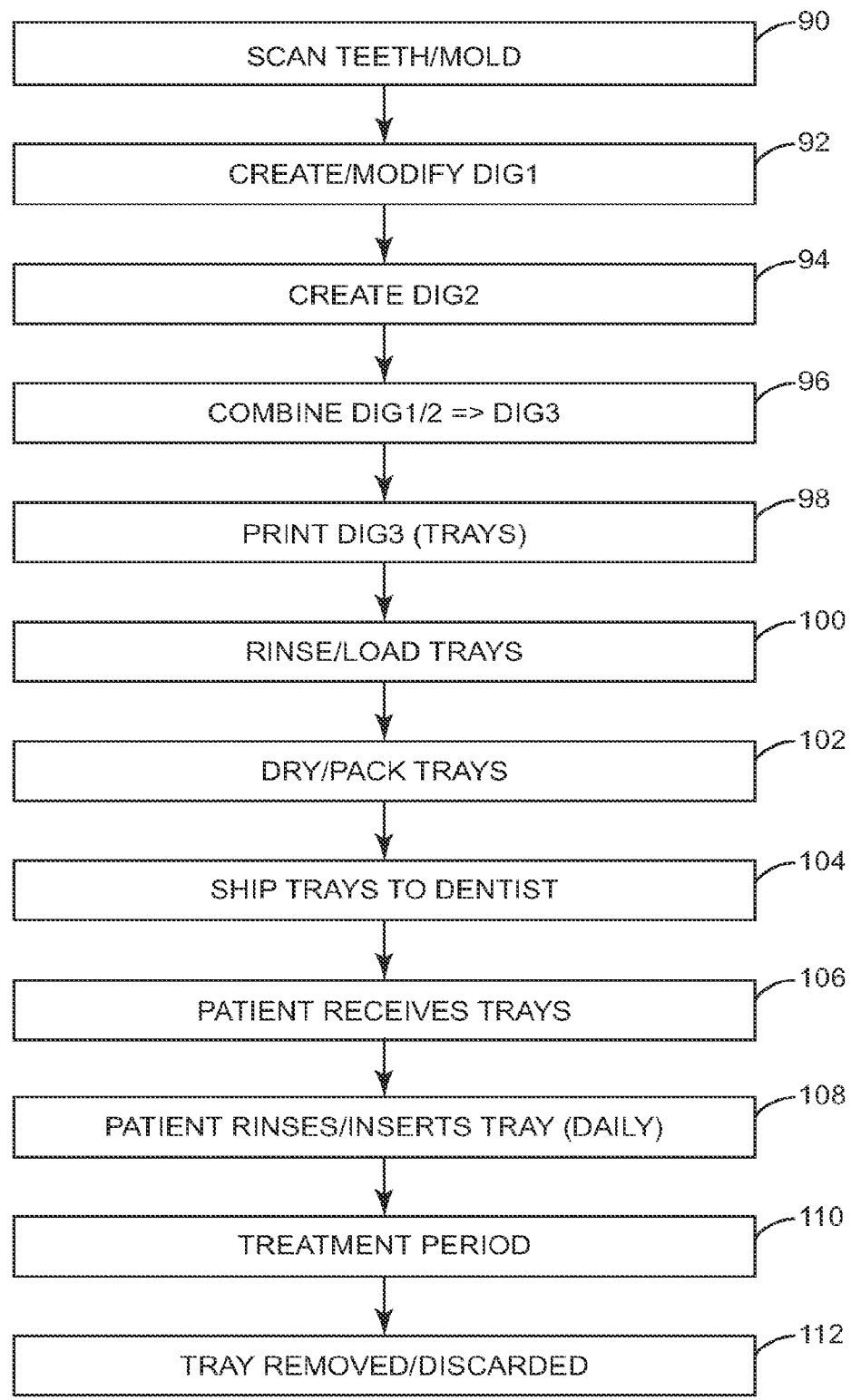
FIG. 8 is a flow chart illustrating an embodiment of the computer-implemented system to generate and manufacture an oral appliance and its use by a prospective patient.

FIG. 8 is a flow chart illustrating an embodiment of the computer-implemented system for treating a patient utilizing an oral appliance produced according to this disclosure. As described above, the oral cavity of the patient is scanned and a mold may be generated in step 90. Based on the information gathered in step 90, Dig1 is generated. Subsequently, a second digital data set is generated via digital segmentation and Dig2 is obtained in step 94. As discussed above, Dig1 and Dig2 digital data sets are combined in step 96 to generate Dig3, which provides the logic and instructions to a 3D printer to print Dig3 in step 98. The oral appliances produced by a stereolithography are then rinsed and loaded with medicaments in step 100. The oral appliances are then dried and packed in step 102 and shipped to a dental professional in step 104. Alternatively, there may be no rinse step or medicament loading as the stereolithography machine may have the medicaments already loaded in its print head. In step 106, the patient receives the oral appliances and inserts them as required in a daily process in step 108. After the treatment period of step 110 is completed, each oral appliance is removed and discarded in step 112. Alternatively, if a diagnosis needs to be made the oral appliances can be sent to a laboratory for testing and then the oral appliances disposed of by the laboratory.

Stereolithography

Stereolithography is the manufacturing process that may be employed for rapidly and accurately producing the oral appliances described herein. A commercially-available stereolithography apparatus (SLA) may be employed to carry out the rapid prototyping methods described herein. In many cases, stereolithography is carried out using a defined amount of liquid UV-curable photopolymer, which can be a "resin" and an ultraviolet (UV) laser to assemble all or a portion of the oral appliance one layer at a time. According to such methods, the laser beam will "trace" a cross-sectional pattern, for each layer of the oral appliance, on the surface of the liquid resin. By exposing the resin to UV energy, the resin solidifies (or "cures") in accordance with the pattern traced by the beam of energy, which adheres to the layer beneath it.

After a pattern has been traced by the beam of UV energy, a so-called elevator platform within the SLA descends by a single layer thickness, typically about 0.05 mm to 0.15. Next, a resin-filled blade traverses across each part of the cross-section, which re-coats the model with new UV-curable resin. On this new layer of resin, the subsequent layer pattern is traced, adhering to the previous layer. This process allows for a complete three-dimensional, real-sized prototyped oral appliance to be produced. After a prototype oral appliance is produced, the oral appliance may, optionally, be cleaned and the excess resin removed therefrom by immersion in a chemical bath and then cured in a UV oven. U.S. Pat. No. 4,575,330 ("Apparatus for Production of Three-Dimensional Objects by Stereolithography") provides a non-limiting method of stereolithography, which may be used in the present application and is hereby incorporated by reference in its entirety. With respect to the oral appliance described herein, the print heads of the SLA can dispense polymers according to instructions provided by Dig1 and Dig2 to generate Dig3 as described above. Accordingly, the viscosity of the polymer, curing rates, feed rates to the print heads can be considered in manufacturing the oral appliances described herein.

An alternate method of stereolithography involves the deposition of successive layers of liquid or powder onto a hard surface, with each layer immediately cured by a beam of UV energy, and in this way builds up the oral appliance from a series of cross sectional patterns of Dig3. These layers, which correspond to the virtual cross section of Dig3, are joined together or fused automatically to create the oral appliance. Further, it will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method of delivering a medicament to the teeth and soft tissues inside the oral cavity, the method comprising: providing an oral appliance comprising an interior surface having a medicament disposed in or on at least a portion of and/or all of the interior surface of the oral appliance, the interior surface being formed to fit contours of at least the portion of the teeth and/or soft tissue areas inside the oral cavity and being configured for supporting and holding the medicament in contact with at least the portion of the teeth and/or soft tissue areas inside the oral cavity to deliver the medicament, wherein the oral appliance is made by a computer implemented method, the computer implemented method comprising creating a digital image of the oral cavity by obtaining a baseline digital image of at least the portion of the teeth and/or soft tissue areas of the oral cavity using an imaging device; obtaining a first digital image of the oral appliance based on the baseline digital image corresponding to the at least the portion of the teeth, and/or soft tissue areas of the oral cavity of the baseline image, creating a second digital image based on the baseline digital image corresponding to at least the portion of the teeth and/or soft tissue areas of the oral cavity in need of treatment with the medicament; combining the first digital image and the second digital image to form a third digital image of the oral appliance that comprises a treatment area for treatment with the medicament and storing the third digital image in the computer; instructing a 3D printer to produce the oral appliance from at least the stored third digital image; producing the oral appliance having a medicament disposed in or on at least a portion and/or all of the interior surface and delivering the medicament to the teeth and soft tissues inside the oral cavity.

2. A method of delivering a medicament of claim 1, wherein the oral appliance comprises a hydrogel.

3. A method of delivering a medicament of claim 2, wherein the oral appliance further comprises a brush polymer, gingival cells or a combination thereof.

4. A method of delivering a medicament of claim 2, wherein the hydrogel comprises about 10% to about 90% by weight of the oral appliance; the hydrogel comprises about 20% to about 80% by weight of the oral appliance; the hydrogel comprises about 30% to about 70% by weight of the oral appliance; or the hydrogel comprises about 40% to about 60% by weight of the oral appliance; or the medicament comprises about 0.01% to about 50% of the oral appliance; the medicament comprises about 0.1% to about 20% by weight of the oral appliance, or the medicament comprises about 0.5% to about 10% by weight of the oral appliance; or the medicament comprises about 1% to about 7% by weight of the oral appliance.

5. A method of delivering a medicament of claim 1, wherein the oral appliance is monolithic.

6. A method of delivering a medicament of claim 1, wherein the oral appliance has a thickness of from about 0.06 inches to about 0.2 inches.

7. A method of delivering a medicament of claim 6, wherein the thickness of surface oral appliance is incrementally configured for treatment of a gum disease.

8. A method of delivering a medicament of claim 1, wherein the medicament is delivered using at least two of the oral appliances.

9. A method of delivering a medicament of claim 1, wherein the oral appliance comprises an external surface having a bulge or a rough area, the bulge comprising a medicament for delivery into the blood stream through lingual veins, the rough area having a medicament for delivery to the papillae of the tongue.

10. A method of delivering a medicament of claim 1, wherein the oral appliance comprises tissue for grafting a cleft palate or other defects of the jaws and face.

11. A method of delivering a medicament of claim 1, wherein an internal surface comprises medicament disposed in it at discrete positions and contacts an oral soft tissue and extends to at least one of (i) a muco-gingival junction; (ii) at least 2 mm to 5 mm buccally beyond a gingival margin; or (iii) at least 2 mm to 5 mm lingually beyond a gingival margin.

12. A method of delivering a medicament of claim 11, wherein the oral appliance comprises medicament disposed uniformly throughout the internal surface and the oral appliance delivers at least one of (i) a bolus dose of the medicament; (ii) a single dose of the medicament; or (iii) multiple doses of the medicament.

13. A method of delivering a medicament of claim 1, the medicament comprises at least one analgesic, whitening agent, breath freshener, anti-inflammatory, anticalculus agent, antimicrobial, anesthetic, muscle relaxant, selective H-2 antagonists, anticaries agent, nutrient, vitamin, mineral, herbal product, cell, or combinations thereof.

14. A method of delivering a medicament of claim 1, wherein the oral appliance is constructed to represent all of a patient's teeth and/or soft tissue areas inside the oral cavity.

15. A method of delivering a medicament to the teeth and soft tissues inside the oral cavity, the method comprising providing an oral appliance comprising an interior surface having a medicament disposed in or on at least a portion of and/or all of the interior surface of the oral appliance, the interior surface being formed to fit contours of at least the portion of the teeth and/or soft tissue areas inside the oral cavity and being configured for supporting and holding the medicament in contact with at least the portion of the teeth and/or soft tissue areas inside the oral cavity to deliver the medicament, wherein the oral appliance is produced by a computer implemented method, the computer implemented method comprising generating first digital data representing a first virtual layer overlying and conforming to a baseline digital image which is a digitally stored topography of the oral cavity produced by an imaging device; generating a second digital data from the baseline digital image by performing a digital segmentation defining at least one treatment surface area including discrete regions of the oral cavity in need of treatment, and producing said second digital data so as to represent a second virtual layer circumscribed by said at least one treatment surface area and including a volume extending into said topography; combining the first digital data and the second digital data to form third digital data representing said first virtual layer having a surface with said at least one second virtual layer added onto the surface and being configured to direct a 3D printer, wherein the treatment surface comprises discrete regions where at least one medicament is to be placed; directing the 3D printer to produce the oral appliance containing the at least one medicament; and producing the oral appliance having a medicament disposed in or on at least a portion and/or all of the interior surface.

16. A method of claim 15, wherein the computer creates a virtual 3D image of the oral appliance indicating the at least one oral treatment surface requiring treatment in the oral cavity; and displays on a display the virtual 3D image; and performs interactive treatment plans including the selection of the at least one medicament.

* * * * *